(12) United States Patent
Liu et al.

(10) Patent No.: US 10,975,377 B2
(45) Date of Patent: Apr. 13, 2021

(54) METHOD FOR REGULATING EXPRESSION OF PROTEIN OF INTEREST IN BACILLUS SUBTILIS

(71) Applicant: Jiangnan University, Wuxi (CN)

(72) Inventors: Yanfeng Liu, Wuxi (CN); Guocheng Du, Wuxi (CN); Rongzhen Tian, Wuxi (CN); Jian Chen, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 16/255,054

(22) Filed: Jan. 23, 2019

(65) Prior Publication Data

US 2019/0233830 A1 Aug. 1, 2019

(30) Foreign Application Priority Data

Jan. 30, 2018 (CN) .......................... 201810091280.X
Aug. 29, 2018 (CN) .......................... 201810992061.9
Oct. 24, 2018 (CN) .......................... 201811241708.0

(51) Int. Cl.
*C12N 15/75* (2006.01)
*C07K 14/435* (2006.01)

(52) U.S. Cl.
CPC ........ *C12N 15/75* (2013.01); *C07K 14/43504* (2013.01)

(58) Field of Classification Search
None
See application file for complete search history.

(56) References Cited

FOREIGN PATENT DOCUMENTS

WO WO-8702385 A1 * 4/1987 ............. C07K 14/62

OTHER PUBLICATIONS

Zhang et al. Applied and Environmental Microbiology, Jul. 2005, vol. 71, No. 7 p. 4101-4103.*

* cited by examiner

*Primary Examiner* — Oluwatosin A Ogunbiyi
(74) *Attorney, Agent, or Firm* — IPro, PLLC

(57) ABSTRACT

The present disclosure relates to a method for regulating expression of protein of interest in *Bacillus subtilis*, and belongs to the technical field of genetic engineering. The method comprises: using *Bacillus subtilis* as an expression host, adding the N-terminal nucleotide sequence coding the first 15 amino acids of the endogenous protein before the coding gene of the protein of interest or modifying the original N-terminal nucleotide sequence coding the first 15 amino acids, and performing free expression in plasmid, thereby regulating expression of the protein of interest in *Bacillus subtilis*, and even regulating the expression difference in different growth phases and the expression level.

5 Claims, 11 Drawing Sheets

Specification includes a Sequence Listing.

SEQUENCE LISTING

```
<160> NUMBER OF SEQ ID NOS: 164

<210> SEQ ID NO 1
<211> LENGTH: 45
<212> TYPE: DNA
<213> ORGANISM: Bacillus subtilis

<400> SEQUENCE: 1
atgaacaaaa cagaacttat caatgcggtt gcagaagcaa gcgaa            45

<210> SEQ ID NO 2
<211> LENGTH: 45
<212> TYPE: DNA
<213> ORGANISM: Bacillus subtilis

<400> SEQUENCE: 2
atgtcacaac aaacaacacc cgcagaacaa aaatcacttc aaaga            45

<210> SEQ ID NO 3
<211> LENGTH: 45
```

<212> TYPE: DNA
<213> ORGANISM: Bacillus subtilis

<400> SEQUENCE: 3
atgctgacac tgaataatat ttcgaagtcg tacaagctgg gaaaa          45

<210> SEQ ID NO 4
<211> LENGTH: 45
<212> TYPE: DNA
<213> ORGANISM: Bacillus subtilis

<400> SEQUENCE: 4
atgaagcata tttatgagaa aggaacatct gacaacgtac ttttg          45

<210> SEQ ID NO 5
<211> LENGTH: 45
<212> TYPE: DNA
<213> ORGANISM: Bacillus subtilis

<400> SEQUENCE: 5
atggctacaa ttcgaattca tgatgaggca aatacaacga ttgaa          45

<210> SEQ ID NO 6
<211> LENGTH: 45
<212> TYPE: DNA
<213> ORGANISM: Bacillus subtilis

<400> SEQUENCE: 6
atgatgatgg gagtcacaaa aacaccttta tacgaaacgt taaat          45

<210> SEQ ID NO 7
<211> LENGTH: 45
<212> TYPE: DNA
<213> ORGANISM: Bacillus subtilis

<400> SEQUENCE: 7
atgaaaaata cgatgaaaag gatgttttgc agcatgacgg ttttg          45

<210> SEQ ID NO 8
<211> LENGTH: 45
<212> TYPE: DNA
<213> ORGANISM: Bacillus subtilis

<400> SEQUENCE: 8
atgaatcagc aagacattaa acaaaaagtg cttgatgttc tagat          45

<210> SEQ ID NO 9
<211> LENGTH: 45
<212> TYPE: DNA
<213> ORGANISM: Bacillus subtilis

<400> SEQUENCE: 9
atgagcttag caccacacgg aggaacatta gtaaacagag tagat          45

<210> SEQ ID NO 10
<211> LENGTH: 45
<212> TYPE: DNA
<213> ORGANISM: Bacillus subtilis

<400> SEQUENCE: 10
atgtcacagc acgttgaaac gaaattagct caaattggga accgt          45

<210> SEQ ID NO 11

```
<211> LENGTH: 45
<212> TYPE: DNA
<213> ORGANISM: Bacillus subtilis

<400> SEQUENCE: 11
atgttgtttg acactcacgc gcatttaaat gcagaacaat atgat            45

<210> SEQ ID NO 12
<211> LENGTH: 45
<212> TYPE: DNA
<213> ORGANISM: Bacillus subtilis

<400> SEQUENCE: 12
atgcttggaa ttttaaataa aatgtttgat ccaacaaaac gtacg            45

<210> SEQ ID NO 13
<211> LENGTH: 45
<212> TYPE: DNA
<213> ORGANISM: Bacillus subtilis

<400> SEQUENCE: 13
atgtcagata tggtaaaaat cacatttcct gatggagcag tcaag            45

<210> SEQ ID NO 14
<211> LENGTH: 45
<212> TYPE: DNA
<213> ORGANISM: Bacillus subtilis

<400> SEQUENCE: 14
gtgccaacaa gtttaaaaga tactgtaaag ttacataacg gagtt            45

<210> SEQ ID NO 15
<211> LENGTH: 45
<212> TYPE: DNA
<213> ORGANISM: Bacillus subtilis

<400> SEQUENCE: 15
ttgaaaacag gttactttt attagaagac gggaacaaaa ttgaa             45

<210> SEQ ID NO 16
<211> LENGTH: 45
<212> TYPE: DNA
<213> ORGANISM: Bacillus subtilis

<400> SEQUENCE: 16
atggctaaag aaaaattcga catgagtaaa ggagaagaac ttttc            45

<210> SEQ ID NO 17
<211> LENGTH: 45
<212> TYPE: DNA
<213> ORGANISM: Bacillus subtilis

<400> SEQUENCE: 17
atggtagtag gagatttccc tattgaaaca gatactcttg taatt            45

<210> SEQ ID NO 18
<211> LENGTH: 45
<212> TYPE: DNA
<213> ORGANISM: Bacillus subtilis

<400> SEQUENCE: 18
atgaaaaaaa tcacaacaaa cgaacaattt aatgaactga ttcaa            45
```

```
<210> SEQ ID NO 19
<211> LENGTH: 45
<212> TYPE: DNA
<213> ORGANISM: Bacillus subtilis

<400> SEQUENCE: 19
atggaaatga tgattaaaaa aagaattaaa caagtcaaaa aaggc            45

<210> SEQ ID NO 20
<211> LENGTH: 45
<212> TYPE: DNA
<213> ORGANISM: Bacillus subtilis

<400> SEQUENCE: 20
atgagaatta accacaatat tgcagcgctt aacacactga accgt            45

<210> SEQ ID NO 21
<211> LENGTH: 45
<212> TYPE: DNA
<213> ORGANISM: Bacillus subtilis

<400> SEQUENCE: 21
atgtttatga atctactgg tattgtacgt aaagttgatg aatta             45

<210> SEQ ID NO 22
<211> LENGTH: 45
<212> TYPE: DNA
<213> ORGANISM: Bacillus subtilis

<400> SEQUENCE: 22
atgaatataa atgttgatgt gaagcaaaac gagaatgata tacaa            45

<210> SEQ ID NO 23
<211> LENGTH: 45
<212> TYPE: DNA
<213> ORGANISM: Bacillus subtilis

<400> SEQUENCE: 23
atgaactata acatcagagg agaaaatatt gaagtgacac ccgcg            45

<210> SEQ ID NO 24
<211> LENGTH: 45
<212> TYPE: DNA
<213> ORGANISM: Bacillus subtilis

<400> SEQUENCE: 24
atggcaaagt acactagaga agatatcgaa aaattagtaa aagaa            45

<210> SEQ ID NO 25
<211> LENGTH: 45
<212> TYPE: DNA
<213> ORGANISM: Bacillus subtilis

<400> SEQUENCE: 25
atggtaaaag tatattataa cggtgatatc aaagagaacg tattg            45

<210> SEQ ID NO 26
<211> LENGTH: 45
<212> TYPE: DNA
<213> ORGANISM: Bacillus subtilis

<400> SEQUENCE: 26
atgcaaaacg gtaaagtaaa atggttcaac aacgaaaaag gattc            45
```

<210> SEQ ID NO 27
<211> LENGTH: 45
<212> TYPE: DNA
<213> ORGANISM: Bacillus subtilis

<400> SEQUENCE: 27
atggaaacga atgaacaaac aatgccgacg aaatatgatc cggca        45

<210> SEQ ID NO 28
<211> LENGTH: 45
<212> TYPE: DNA
<213> ORGANISM: Bacillus subtilis

<400> SEQUENCE: 28
atggctaaag aaaaattcga ccgttccaaa tcacatgcca atatt        45

<210> SEQ ID NO 29
<211> LENGTH: 45
<212> TYPE: DNA
<213> ORGANISM: Bacillus subtilis

<400> SEQUENCE: 29
atgattacga aaactagcaa aaatgctgct cgtcttaaaa gacac        45

<210> SEQ ID NO 30
<211> LENGTH: 45
<212> TYPE: DNA
<213> ORGANISM: Bacillus subtilis

<400> SEQUENCE: 30
atgtcagaac agaaaaaagt cgtattagca tactcaggag gtctt        45

<210> SEQ ID NO 31
<211> LENGTH: 45
<212> TYPE: DNA
<213> ORGANISM: Bacillus subtilis

<400> SEQUENCE: 31
atgagaaacg aacgcagaaa aaagaaaaaa actttattac tgaca        45

<210> SEQ ID NO 32
<211> LENGTH: 45
<212> TYPE: DNA
<213> ORGANISM: Bacillus subtilis

<400> SEQUENCE: 32
atgagtataa acataaaagc agtaactgat gataatcgtg ctgca        45

<210> SEQ ID NO 33
<211> LENGTH: 45
<212> TYPE: DNA
<213> ORGANISM: Bacillus subtilis

<400> SEQUENCE: 33
atgtttaagc acacaaaaat gctgcagcat cctgctaaac cagat        45

<210> SEQ ID NO 34
<211> LENGTH: 45
<212> TYPE: DNA
<213> ORGANISM: Bacillus subtilis

<400> SEQUENCE: 34
atggcagaca taacaaaat gagcagagaa gaagcaggta gaaaa        45

<210> SEQ ID NO 35
<211> LENGTH: 45
<212> TYPE: DNA
<213> ORGANISM: Bacillus subtilis

<400> SEQUENCE: 35
atggctgaat ggaaaacaaa acggacatac gatgagatat tgtat                45

<210> SEQ ID NO 36
<211> LENGTH: 45
<212> TYPE: DNA
<213> ORGANISM: Bacillus subtilis

<400> SEQUENCE: 36
atgttagaag gtaaagtaaa atggttcaac tctgaaaaag gtttc                45

<210> SEQ ID NO 37
<211> LENGTH: 45
<212> TYPE: DNA
<213> ORGANISM: Bacillus subtilis

<400> SEQUENCE: 37
atgtcattaa gagaagaagc attacacctg cataaagtca accag                45

<210> SEQ ID NO 38
<211> LENGTH: 45
<212> TYPE: DNA
<213> ORGANISM: Bacillus subtilis

<400> SEQUENCE: 38
atggctcaac aaacgaatgt tgcaggacaa aaaacagaaa aacaa                45

<210> SEQ ID NO 39
<211> LENGTH: 45
<212> TYPE: DNA
<213> ORGANISM: Bacillus subtilis

<400> SEQUENCE: 39
atgtctgatt caaatcttac gaatcctata aaagcatttt ttcat                45

<210> SEQ ID NO 40
<211> LENGTH: 45
<212> TYPE: DNA
<213> ORGANISM: Bacillus subtilis

<400> SEQUENCE: 40
atgaggaaaa cagtcattgt aagtgctgca agaactccat ttggc                45

<210> SEQ ID NO 41
<211> LENGTH: 45
<212> TYPE: DNA
<213> ORGANISM: Bacillus subtilis

<400> SEQUENCE: 41
atgagaagct atgaaaaatc aaaaacggct tttaagaagg cgcaa                45

<210> SEQ ID NO 42
<211> LENGTH: 45
<212> TYPE: DNA
<213> ORGANISM: Bacillus subtilis

<400> SEQUENCE: 42
ttgaatcaaa aagctgtcat tctcgacgaa caggcaatta gacgg    45

<210> SEQ ID NO 43
<211> LENGTH: 45
<212> TYPE: DNA
<213> ORGANISM: Bacillus subtilis

<400> SEQUENCE: 43
atggccaaaa taaaagatga ttgtatagaa cttgaattaa caccg    45

<210> SEQ ID NO 44
<211> LENGTH: 45
<212> TYPE: DNA
<213> ORGANISM: Bacillus subtilis

<400> SEQUENCE: 44
atgaccatta aacgtgcatt aatcagtgtt tcagataaaa caaat    45

<210> SEQ ID NO 45
<211> LENGTH: 45
<212> TYPE: DNA
<213> ORGANISM: Bacillus subtilis

<400> SEQUENCE: 45
atggcagaca cattagagcg tgtaacgaaa atcatcgtag atcgc    45

<210> SEQ ID NO 46
<211> LENGTH: 45
<212> TYPE: DNA
<213> ORGANISM: Bacillus subtilis

<400> SEQUENCE: 46
atggcactat ttacagcaaa agtaaccgcg cgaggcggac gagca    45

<210> SEQ ID NO 47
<211> LENGTH: 45
<212> TYPE: DNA
<213> ORGANISM: Bacillus subtilis

<400> SEQUENCE: 47
atgggacttt tagaagattt gcaaagacag gtgttaatcg gtgac    45

<210> SEQ ID NO 48
<211> LENGTH: 45
<212> TYPE: DNA
<213> ORGANISM: Bacillus subtilis

<400> SEQUENCE: 48
atggcaggat taattcgtgt cacacccgaa gagctaagag cgatg    45

<210> SEQ ID NO 49
<211> LENGTH: 45
<212> TYPE: DNA
<213> ORGANISM: Bacillus subtilis

<400> SEQUENCE: 49
atgactaaac aaacaattcg cgttgaattg acatcaacaa aaaaa    45

<210> SEQ ID NO 50
<211> LENGTH: 45
<212> TYPE: DNA
<213> ORGANISM: Bacillus subtilis

<400> SEQUENCE: 50
atgacccatt catttgctgt tccacgttct gttgaatgga aagaa    45

<210> SEQ ID NO 51
<211> LENGTH: 45
<212> TYPE: DNA
<213> ORGANISM: Bacillus subtilis

<400> SEQUENCE: 51
atggaacctt tgaaatcaca tacggggaaa gcagccgtat taaat    45

<210> SEQ ID NO 52
<211> LENGTH: 45
<212> TYPE: DNA
<213> ORGANISM: Bacillus subtilis

<400> SEQUENCE: 52
atgaaaaaaa ttccggttac cgtactgagc ggttatctcg gtgcg    45

<210> SEQ ID NO 53
<211> LENGTH: 45
<212> TYPE: DNA
<213> ORGANISM: Bacillus subtilis

<400> SEQUENCE: 53
atgtgccaat ccaatcaaat tgtcagccat tttttatccc atcga    45

<210> SEQ ID NO 54
<211> LENGTH: 45
<212> TYPE: DNA
<213> ORGANISM: Bacillus subtilis

<400> SEQUENCE: 54
atgtctttaa tcggtaaaga agtacttcca ttcgaagcaa aagca    45

<210> SEQ ID NO 55
<211> LENGTH: 45
<212> TYPE: DNA
<213> ORGANISM: Bacillus subtilis

<400> SEQUENCE: 55
atggctgcaa aacaagaacg ctggcgagag ctcgctgaag taaaa    45

<210> SEQ ID NO 56
<211> LENGTH: 45
<212> TYPE: DNA
<213> ORGANISM: Bacillus subtilis

<400> SEQUENCE: 56
atgtcgtttt tcagaaatca attagcgaat gtagtagagt gggaa    45

<210> SEQ ID NO 57
<211> LENGTH: 45
<212> TYPE: DNA
<213> ORGANISM: Bacillus subtilis

<400> SEQUENCE: 57
atgtttcaaa atagtatgaa acaacgaatg aattgggaag atttt    45

<210> SEQ ID NO 58
<211> LENGTH: 45
<212> TYPE: DNA
<213> ORGANISM: Bacillus subtilis -continued

<400> SEQUENCE: 58
atggcagcaa aatttgaagt gggcagtgtt tacactggta aagtt    45

<210> SEQ ID NO 59
<211> LENGTH: 45
<212> TYPE: DNA
<213> ORGANISM: Bacillus subtilis

<400> SEQUENCE: 59
atggtgacca aaattctaaa agcaccggac ggctctccaa gtgat    45

<210> SEQ ID NO 60
<211> LENGTH: 45
<212> TYPE: DNA
<213> ORGANISM: Bacillus subtilis

<400> SEQUENCE: 60
atgaccaaag gaatcttagg aagaaaaatt ggtatgacgc aagta    45

<210> SEQ ID NO 61
<211> LENGTH: 45
<212> TYPE: DNA
<213> ORGANISM: Bacillus subtilis

<400> SEQUENCE: 61
atgacaacca tcaaaacatc gaatttagga tttccgagaa tcgga    45

<210> SEQ ID NO 62
<211> LENGTH: 45
<212> TYPE: DNA
<213> ORGANISM: Bacillus subtilis

<400> SEQUENCE: 62
ttgatgtcga accagactgt ataccagttc attgccgaaa atcaa    45

<210> SEQ ID NO 63
<211> LENGTH: 45
<212> TYPE: DNA
<213> ORGANISM: Bacillus subtilis

<400> SEQUENCE: 63
atggctttaa atatcgaaga aatcattgct tccgttaaag aagca    45

<210> SEQ ID NO 64
<211> LENGTH: 45
<212> TYPE: DNA
<213> ORGANISM: Bacillus subtilis

<400> SEQUENCE: 64
atgagaatgc gccacaagcc ttgggctgat gacttttttgg ctgaa    45

<210> SEQ ID NO 65
<211> LENGTH: 45
<212> TYPE: DNA
<213> ORGANISM: Bacillus subtilis

<400> SEQUENCE: 65
ttgaggaaag atgaaatcat gcatatcgta tcatgcgcag atgat    45

<210> SEQ ID NO 66
<211> LENGTH: 45
<212> TYPE: DNA
<213> ORGANISM: Bacillus subtilis

<400> SEQUENCE: 66
atggatgcgc ttattgagga agttgatggc atttcaaatc gtact                45

<210> SEQ ID NO 67
<211> LENGTH: 45
<212> TYPE: DNA
<213> ORGANISM: Bacillus subtilis

<400> SEQUENCE: 67
atggcacata gaattttaat tgtagatgac gcagcattta tgcga                45

<210> SEQ ID NO 68
<211> LENGTH: 45
<212> TYPE: DNA
<213> ORGANISM: Bacillus subtilis

<400> SEQUENCE: 68
atgggtctta ttgtacaaaa attcggaggc acttccgtcg gctca                45

<210> SEQ ID NO 69
<211> LENGTH: 45
<212> TYPE: DNA
<213> ORGANISM: Bacillus subtilis

<400> SEQUENCE: 69
atgagcagct tgtttcaaac ctacggccgt tgggatattg acatc                45

<210> SEQ ID NO 70
<211> LENGTH: 45
<212> TYPE: DNA
<213> ORGANISM: Bacillus subtilis

<400> SEQUENCE: 70
atggcaaaag tattatatat cactgctcat ccacatgacg aagca                45

<210> SEQ ID NO 71
<211> LENGTH: 45
<212> TYPE: DNA
<213> ORGANISM: Bacillus subtilis

<400> SEQUENCE: 71
atgattatct gtaaaacccc acgtgaactt ggtatcatgc gggaa                45

<210> SEQ ID NO 72
<211> LENGTH: 45
<212> TYPE: DNA
<213> ORGANISM: Bacillus subtilis

<400> SEQUENCE: 72
atgaaacgag ataaggtgca gaccttacat ggagaaatac atatt                45

<210> SEQ ID NO 73
<211> LENGTH: 45
<212> TYPE: DNA
<213> ORGANISM: Bacillus subtilis

<400> SEQUENCE: 73
atgtctatgc ataaagcact caccattgcc ggctcagatt ccagc                45

<210> SEQ ID NO 74
<211> LENGTH: 45
<212> TYPE: DNA

<213> ORGANISM: Bacillus subtilis

<400> SEQUENCE: 74
atggtgacaa cggtgcagcg tacgttccga aaggaagttc tacat            45

<210> SEQ ID NO 75
<211> LENGTH: 45
<212> TYPE: DNA
<213> ORGANISM: Bacillus subtilis

<400> SEQUENCE: 75
ttgaagaaac gtattgctct attgcccgga gacgggatcg ccct            45

<210> SEQ ID NO 76
<211> LENGTH: 45
<212> TYPE: DNA
<213> ORGANISM: Bacillus subtilis

<400> SEQUENCE: 76
atgaacgacc aatcctgtgt aagaatcatg acagaatggg atatt            45

<210> SEQ ID NO 77
<211> LENGTH: 45
<212> TYPE: DNA
<213> ORGANISM: Bacillus subtilis

<400> SEQUENCE: 77
gtggcacaag gtgaaaaaat tacagtctct aacggagtat taaac            45

<210> SEQ ID NO 78
<211> LENGTH: 45
<212> TYPE: DNA
<213> ORGANISM: Bacillus subtilis

<400> SEQUENCE: 78
atgatacgaa gtatgacagg cttcggcagt gcaagcaaaa cacaa            45

<210> SEQ ID NO 79
<211> LENGTH: 45
<212> TYPE: DNA
<213> ORGANISM: Bacillus subtilis

<400> SEQUENCE: 79
gtgacaaatc gcgatattgt atggcatgaa gcctctatca caaaa            45

<210> SEQ ID NO 80
<211> LENGTH: 45
<212> TYPE: DNA
<213> ORGANISM: Bacillus subtilis

<400> SEQUENCE: 80
ttgttattta aaaagacag aaaacaagaa acagcttact tttca            45

<210> SEQ ID NO 81
<211> LENGTH: 45
<212> TYPE: DNA
<213> ORGANISM: Bacillus subtilis

<400> SEQUENCE: 81
ttgaaaatag gaattgtagg tgctacagga tatggaggca ccgaa            45

<210> SEQ ID NO 82
<211> LENGTH: 45

```
<212> TYPE: DNA
<213> ORGANISM: Bacillus subtilis

<400> SEQUENCE: 82
ttgagtaaac acaattggac gctggaaacc cagctcgtgc acaat            45

<210> SEQ ID NO 83
<211> LENGTH: 45
<212> TYPE: DNA
<213> ORGANISM: Bacillus subtilis

<400> SEQUENCE: 83
gtgaagtttt cagaagaatg ccgcagtgca gccgcagaat ggtgg            45

<210> SEQ ID NO 84
<211> LENGTH: 45
<212> TYPE: DNA
<213> ORGANISM: Bacillus subtilis

<400> SEQUENCE: 84
atgtacatat ttcaagctga tcagcttagt gccaaagaca catac            45

<210> SEQ ID NO 85
<211> LENGTH: 45
<212> TYPE: DNA
<213> ORGANISM: Bacillus subtilis

<400> SEQUENCE: 85
gtgaaaaata aatggctgtc ttttttttcg ggtaaggtcc agctt            45

<210> SEQ ID NO 86
<211> LENGTH: 45
<212> TYPE: DNA
<213> ORGANISM: Bacillus subtilis

<400> SEQUENCE: 86
atgaaaacag actggtggaa ggatgcagtg gtgtaccaaa tttac            45

<210> SEQ ID NO 87
<211> LENGTH: 45
<212> TYPE: DNA
<213> ORGANISM: Bacillus subtilis

<400> SEQUENCE: 87
atgagaaagt acgaagttat gtacattatc cgcccaaaca ttgac            45

<210> SEQ ID NO 88
<211> LENGTH: 45
<212> TYPE: DNA
<213> ORGANISM: Bacillus subtilis

<400> SEQUENCE: 88
gtggaagtta ctgacgtaag attacgccgc gtgaataccg atggt            45

<210> SEQ ID NO 89
<211> LENGTH: 45
<212> TYPE: DNA
<213> ORGANISM: Bacillus subtilis

<400> SEQUENCE: 89
atggcgcaaa tgacaatgat tcaagcaatc acggatgcgt tacgc            45

<210> SEQ ID NO 90
```

```
<211> LENGTH: 45
<212> TYPE: DNA
<213> ORGANISM: Bacillus subtilis

<400> SEQUENCE: 90
atgaaaaaaa aaccgttaac tcctagacag attgtagatc ggtta          45

<210> SEQ ID NO 91
<211> LENGTH: 45
<212> TYPE: DNA
<213> ORGANISM: Artificial Sequence
<220> FEATURE:
<223> OTHER INFORMATION: Synthetic DNA

<400> SEQUENCE: 91
atgaacaaag aaacaaaga aacaaagaa acaaagaaa acaaa              45

<210> SEQ ID NO 92
<211> LENGTH: 45
<212> TYPE: DNA
<213> ORGANISM: Artificial Sequence
<220> FEATURE:
<223> OTHER INFORMATION: Synthetic DNA

<400> SEQUENCE: 92
atgaacaaca aaaagaaga aacaacaaa aagaagaaa acaac              45

<210> SEQ ID NO 93
<211> LENGTH: 45
<212> TYPE: DNA
<213> ORGANISM: Artificial Sequence
<220> FEATURE:
<223> OTHER INFORMATION: Synthetic DNA

<400> SEQUENCE: 93
atgaacaaca acaaaaaaaa agaagaagaa aacaacaaca aaaaa           45

<210> SEQ ID NO 94
<211> LENGTH: 45
<212> TYPE: DNA
<213> ORGANISM: Artificial Sequence
<220> FEATURE:
<223> OTHER INFORMATION: Synthetic DNA

<400> SEQUENCE: 94
atgaacaaaa aaaaaaaga aaaaaaaaaa aacaacaaag aaaaa            45

<210> SEQ ID NO 95
<211> LENGTH: 45
<212> TYPE: DNA
<213> ORGANISM: Artificial Sequence
<220> FEATURE:
<223> OTHER INFORMATION: Synthetic DNA

<400> SEQUENCE: 95
atgaaaaacg aaaaaaaaaa agaagaaaaa aacaacaaag aaaaa           45

<210> SEQ ID NO 96
<211> LENGTH: 45
<212> TYPE: DNA
<213> ORGANISM: Artificial Sequence
<220> FEATURE:
<223> OTHER INFORMATION: Synthetic DNA

<400> SEQUENCE: 96
atgaacaaaa aagaaaaaga aaacaaaaac aacgaaaaaa aaaac           45
```

<210> SEQ ID NO 97
<211> LENGTH: 45
<212> TYPE: DNA
<213> ORGANISM: Artificial Sequence
<220> FEATURE:
<223> OTHER INFORMATION: Synthetic DNA

<400> SEQUENCE: 97
atgaacatca aagtagaaac aaaccaaaaa atcgaagtaa acaca                45

<210> SEQ ID NO 98
<211> LENGTH: 45
<212> TYPE: DNA
<213> ORGANISM: Artificial Sequence
<220> FEATURE:
<223> OTHER INFORMATION: Synthetic DNA

<400> SEQUENCE: 98
atgaacaaca tcaaaaaagt agaagaaaca aacaaccaaa aaaaa                45

<210> SEQ ID NO 99
<211> LENGTH: 45
<212> TYPE: DNA
<213> ORGANISM: Artificial Sequence
<220> FEATURE:
<223> OTHER INFORMATION: Synthetic DNA

<400> SEQUENCE: 99
atgaaaaaaa tcaacaacgt agaagaaaca aaaaaacaaa acaac                45

<210> SEQ ID NO 100
<211> LENGTH: 45
<212> TYPE: DNA
<213> ORGANISM: Artificial Sequence
<220> FEATURE:
<223> OTHER INFORMATION: Synthetic DNA

<400> SEQUENCE: 100
atgaacaaaa tcaaagaagt agaaaacaca aacaaacaaa aagaa                45

<210> SEQ ID NO 101
<211> LENGTH: 45
<212> TYPE: DNA
<213> ORGANISM: Artificial Sequence
<220> FEATURE:
<223> OTHER INFORMATION: Synthetic DNA

<400> SEQUENCE: 101
atgaacaaca acatcaaaaa aaaagtagaa gaagaaacaa acaac                45

<210> SEQ ID NO 102
<211> LENGTH: 45
<212> TYPE: DNA
<213> ORGANISM: Bacillus subtilis

<400> SEQUENCE: 102
atgaaaaaaa tcatcaacaa cgtagtaaaa aaacaacaa acaac                 45

<210> SEQ ID NO 103
<211> LENGTH: 45
<212> TYPE: DNA
<213> ORGANISM: Bacillus subtilis

<400> SEQUENCE: 103
ttgttaaagc cattaggtga tcgcgttgtc attgaactcg tagaa            45

<210> SEQ ID NO 104
<211> LENGTH: 45
<212> TYPE: DNA
<213> ORGANISM: Bacillus subtilis

<400> SEQUENCE: 104
ttgaatggaa acgaacccca cggaggggta ttaatcaacc gctgt            45

<210> SEQ ID NO 105
<211> LENGTH: 45
<212> TYPE: DNA
<213> ORGANISM: Bacillus subtilis

<400> SEQUENCE: 105
ttggcaaaga aagacgaaca cctcagaaag cccgaatggc ttaaa            45

<210> SEQ ID NO 106
<211> LENGTH: 45
<212> TYPE: DNA
<213> ORGANISM: Bacillus subtilis

<400> SEQUENCE: 106
ttggcaaaga aagacgaaca cctcagaaag cccgaatggc ttaaa            45

<210> SEQ ID NO 107
<211> LENGTH: 45
<212> TYPE: DNA
<213> ORGANISM: Bacillus subtilis

<400> SEQUENCE: 107
atggctcgct atacaggtcc atcttggaaa ctgtcccgcc gtcta            45

<210> SEQ ID NO 108
<211> LENGTH: 45
<212> TYPE: DNA
<213> ORGANISM: Bacillus subtilis

<400> SEQUENCE: 108
atgacaatat tagcaattga tacatcaaat tatacattgg gcatt            45

<210> SEQ ID NO 109
<211> LENGTH: 45
<212> TYPE: DNA
<213> ORGANISM: Bacillus subtilis

<400> SEQUENCE: 109
gtgaaaggca caaaaggaaa ggttttttcgt gttttttactg ctttt            45

<210> SEQ ID NO 110
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 110

Met Lys Lys Ile Glu Glu Asn Asn Gln Lys Asn Glu Lys Ile Gln
1               5                   10                  15

<210> SEQ ID NO 111
<211> LENGTH: 15
<212> TYPE: PRT

<213> ORGANISM: Artificial Sequence
<220> FEATURE:
<223> OTHER INFORMATION: Protein translated from synthetic DNA

<400> SEQUENCE: 111

Met Glu Met Met Ile Lys Lys Asn Ile Lys Gln Asn Lys Lys Asn
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 112

Met Lys Ile Lys Asn Asn Ile Glu Glu Gln Asn Thr Lys Asn Arg
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 113

Met Asn Met Lys Lys Thr Asn Ile Val Lys Lys Val Glu Glu Asn
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 114

Met Asn Ile Asn Val Lys Lys Glu Gln Asn Glu Asn Lys Ile Gln
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 115

Met Asn Lys Asn Ile Lys Lys Glu Asn Ile Glu Val Thr Pro Lys
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 116

Met Lys Lys Asn Thr Glu Glu Asn Ile Glu Lys Val Lys Glu
1               5                   10                  15

<210> SEQ ID NO 117
<211> LENGTH: 15
<212> TYPE: PRT
<213> ORGANISM: Artificial Sequence

```
<220> FEATURE:
<223> OTHER INFORMATION: Protein translated from synthetic DNA

<400> SEQUENCE: 117

Leu Lys Lys Gln Asn Asn Ile Lys Glu Val Ile Glu Asn Val Glu
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 118

Leu Asn Gln Asn Glu Pro Lys Lys Gln Val Asn Ile Asn Lys Glu
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 119

Met Asn Lys Lys Gln Glu Glu Asn Asn Lys Pro Glu Gln Ile Lys
1               5                   10                  15

<210> SEQ ID NO 120
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 120

Met Gln Lys Lys Ile Glu Asn Asn Thr Val Glu Gln Lys Lys Phe
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 121

Met Lys Lys Tyr Thr Asn Pro Asn Lys Lys Ile Glu Asn Asn Lys
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 122

Met Lys Ile Asn Asn Ile Lys Thr Lys Asn Tyr Thr Glu Asn Ile
1               5                   10                  15

<210> SEQ ID NO 123
<211> LENGTH: 15
<212> TYPE: PRT
<213> ORGANISM: Artificial Sequence
<220> FEATURE:
```

```
<223> OTHER INFORMATION: Protein translated from synthetic DNA

<400> SEQUENCE: 123

Met Lys Lys Thr Ile Asn Lys Val Phe Asn Asn Phe Thr Lys Phe
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 124

Met Ser Trp Ile Thr Thr Asp Cys Ser Phe Trp Asp Leu Ile Gln
1               5                   10                  15

<210> SEQ ID NO 125
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 125

Met Ser Trp Asp Ile Cys Ser Arg Ile Trp Asp Val Cys Ser Gly
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 126

Met Arg Ile Ser His Trp Ile Ala Ala Leu Asp Thr Leu Cys Arg
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 127

Met Phe Ser Trp Ser Thr Gly Ile Val Arg Asp Val Asp Cys Leu
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 128

Met Ser Ile Trp Val Asp Val Asp Gln Cys Ser Trp Asp Ile Gln
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: Protein translated from synthetic DNA
```

<400> SEQUENCE: 129

Met Ser Tyr Trp Ile Arg Gly Asp Cys Ile Ser Val Thr Pro Ala
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 130

Met Ala Ser Tyr Thr Arg Trp Asp Ile Asp Cys Leu Val Ser Trp
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 131

Met Leu Lys Ile Thr Leu Asn Glu Gln Leu Asn Glu Leu Ile Gln
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 132

Met Leu Lys His Thr Lys Met Leu Gln Leu Pro Ala Lys Pro Asp
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 133

Met Leu Thr Lys Thr Leu Lys Asn Ala Leu Arg Leu Lys Arg His
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 134

Met Leu Asp Asn Asn Leu Met Ser Arg Leu Glu Ala Gly Arg Lys
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 135

Met Leu Asp Ser Asn Leu Thr Asn Pro Leu Lys Ala Phe Phe His
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 136

Met Leu Ser Tyr Glu Leu Ser Lys Thr Leu Phe Lys Glu Ala Gln
1               5                   10                  15

<210> SEQ ID NO 137
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 137

Met Leu Asp Gln Ser Leu Val Arg Ile Leu Thr Glu Trp Asp Ile
1               5                   10                  15

<210> SEQ ID NO 138
<211> LENGTH: 15
<212> TYPE: PRT
<213> ORGANISM: Bacillus subtilis

<400> SEQUENCE: 138

Met Lys Lys Ile Thr Thr Asn Glu Gln Phe Asn Glu Leu Ile Gln
1               5                   10                  15

<210> SEQ ID NO 139
<211> LENGTH: 15
<212> TYPE: PRT
<213> ORGANISM: Bacillus subtilis

<400> SEQUENCE: 139

Met Glu Met Met Ile Lys Lys Arg Ile Lys Gln Val Lys Lys Gly
1               5                   10                  15

<210> SEQ ID NO 140
<211> LENGTH: 15
<212> TYPE: PRT
<213> ORGANISM: Bacillus subtilis

<400> SEQUENCE: 140

Met Arg Ile Asn His Asn Ile Ala Ala Leu Asn Thr Leu Asn Arg
1               5                   10                  15

<210> SEQ ID NO 141
<211> LENGTH: 15
<212> TYPE: PRT
<213> ORGANISM: Bacillus subtilis

<400> SEQUENCE: 141

Met Phe Met Lys Ser Thr Gly Ile Val Arg Lys Val Asp Glu Leu
1               5                   10                  15

<210> SEQ ID NO 142
<211> LENGTH: 15
<212> TYPE: PRT

-continued

<213> ORGANISM: Bacillus subtilis

<400> SEQUENCE: 142

Met Asn Ile Asn Val Asp Val Lys Gln Asn Glu Asn Asp Ile Gln
1               5                   10                  15

<210> SEQ ID NO 143
<211> LENGTH: 15
<212> TYPE: PRT
<213> ORGANISM: Bacillus subtilis

<400> SEQUENCE: 143

Met Asn Tyr Asn Ile Arg Gly Glu Asn Ile Glu Val Thr Pro Ala
1               5                   10                  15

<210> SEQ ID NO 144
<211> LENGTH: 15
<212> TYPE: PRT
<213> ORGANISM: Bacillus subtilis

<400> SEQUENCE: 144

Met Ala Lys Tyr Thr Arg Glu Asp Ile Glu Lys Leu Val Lys Glu
1               5                   10                  15

<210> SEQ ID NO 145
<211> LENGTH: 15
<212> TYPE: PRT
<213> ORGANISM: Bacillus subtilis

<400> SEQUENCE: 145

Leu Leu Lys Pro Leu Gly Asp Arg Val Val Ile Glu Leu Val Glu
1               5                   10                  15

<210> SEQ ID NO 146
<211> LENGTH: 15
<212> TYPE: PRT
<213> ORGANISM: Bacillus subtilis

<400> SEQUENCE: 146

Leu Asn Gly Asn Glu Pro His Gly Gly Val Leu Ile Asn Arg Cys
1               5                   10                  15

<210> SEQ ID NO 147
<211> LENGTH: 15
<212> TYPE: PRT
<213> ORGANISM: Bacillus subtilis

<400> SEQUENCE: 147

Met Ala Lys Lys Asp Glu His Leu Arg Lys Pro Glu Trp Leu Lys
1               5                   10                  15

<210> SEQ ID NO 148
<211> LENGTH: 15
<212> TYPE: PRT
<213> ORGANISM: Bacillus subtilis

<400> SEQUENCE: 148

Met Gln Ala Phe Asp Glu Leu Leu Thr Val Glu Gln Leu Ser Phe
1               5                   10                  15

<210> SEQ ID NO 149
<211> LENGTH: 15
<212> TYPE: PRT
<213> ORGANISM: Bacillus subtilis -continued

<400> SEQUENCE: 149

Met Ala Arg Tyr Thr Gly Pro Ser Trp Lys Leu Ser Arg Arg Leu
1               5                   10                  15

<210> SEQ ID NO 150
<211> LENGTH: 15
<212> TYPE: PRT
<213> ORGANISM: Bacillus subtilis

<400> SEQUENCE: 150

Met Thr Ile Leu Ala Ile Asp Thr Ser Asn Tyr Thr Leu Gly Ile
1               5                   10                  15

<210> SEQ ID NO 151
<211> LENGTH: 15
<212> TYPE: PRT
<213> ORGANISM: Bacillus subtilis

<400> SEQUENCE: 151

Met Lys Gly Thr Lys Gly Lys Val Phe Arg Val Phe Thr Ala Phe
1               5                   10                  15

<210> SEQ ID NO 152
<211> LENGTH: 60
<212> TYPE: DNA
<213> ORGANISM: Artificial Sequence
<220> FEATURE:
<223> OTHER INFORMATION: Synthetic DNA

<400> SEQUENCE: 152
tggttcaacg aaaaaggatt catgagtaaa ggagaagaac ttttcactgg agttgtccca      60

<210> SEQ ID NO 153
<211> LENGTH: 59
<212> TYPE: DNA
<213> ORGANISM: Artificial Sequence
<220> FEATURE:
<223> OTHER INFORMATION: Synthetic DNA

<400> SEQUENCE: 153
tacgccaagc tttcatcact atttgtatag ttcatccatg ccatgtgtaa tcccagcag       59

<210> SEQ ID NO 154
<211> LENGTH: 39
<212> TYPE: DNA
<213> ORGANISM: Artificial Sequence
<220> FEATURE:
<223> OTHER INFORMATION: Synthetic DNA

<400> SEQUENCE: 154
agtgatgaaa gcttggcgta atcatggtca tagctgttt                            39

<210> SEQ ID NO 155
<211> LENGTH: 83
<212> TYPE: DNA
<213> ORGANISM: Artificial Sequence
<220> FEATURE:
<223> OTHER INFORMATION: Synthetic DNA

<400> SEQUENCE: 155
cctttttcgt tgttgaacca ttttacttta ccgttttgca tgtgtacatt cctctcttac      60
ctataatggt accgctatca ctt                                             83

<210> SEQ ID NO 156

```
<211> LENGTH: 22
<212> TYPE: DNA
<213> ORGANISM: Artificial Sequence
<220> FEATURE:
<223> OTHER INFORMATION: Synthetic DNA

<400> SEQUENCE: 156
ttcttgctga gtctggcttt cg                                              22

<210> SEQ ID NO 157
<211> LENGTH: 22
<212> TYPE: DNA
<213> ORGANISM: Artificial Sequence
<220> FEATURE:
<223> OTHER INFORMATION: Synthetic DNA

<400> SEQUENCE: 157
cggctcgtat gttgtgtgga at                                              22

<210> SEQ ID NO 158
<211> LENGTH: 68
<212> TYPE: DNA
<213> ORGANISM: Artificial Sequence
<220> FEATURE:
<223> OTHER INFORMATION: Synthetic DNA

<400> SEQUENCE: 158
gatgattaaa aaaaacatta aacaaaacaa aaaaaacatg agtaaaggag aagaactttt     60
cactggag                                                              68

<210> SEQ ID NO 159
<211> LENGTH: 66
<212> TYPE: DNA
<213> ORGANISM: Artificial Sequence
<220> FEATURE:
<223> OTHER INFORMATION: Synthetic DNA

<400> SEQUENCE: 159
ttacacatgg catggatgaa ctatacaaat agtgatgaaa gcttggcgta atcatggtca     60
tagctg                                                                66

<210> SEQ ID NO 160
<211> LENGTH: 64
<212> TYPE: DNA
<213> ORGANISM: Artificial Sequence
<220> FEATURE:
<223> OTHER INFORMATION: Synthetic DNA

<400> SEQUENCE: 160
tgtttaatgt ttttttttaat catcatttcc atgtgtacat tcctctctta cctataatgg   60
tacc                                                                  64

<210> SEQ ID NO 161
<211> LENGTH: 55
<212> TYPE: DNA
<213> ORGANISM: Artificial Sequence
<220> FEATURE:
<223> OTHER INFORMATION: Synthetic DNA

<400> SEQUENCE: 161
ctgcagttac ctgctaaacc agatatgagt aaaggagaag aacttttcac tggag          55

<210> SEQ ID NO 162
<211> LENGTH: 70
```

```
<212> TYPE: DNA
<213> ORGANISM: Artificial Sequence
<220> FEATURE:
<223> OTHER INFORMATION: Synthetic DNA

<400> SEQUENCE: 162
cgatatcttc tctagtgtac tttgccatgt gtacattcct ctcttaccta taatggtacc    60
gctatcactt                                                            70

<210> SEQ ID NO 163
<211> LENGTH: 73
<212> TYPE: DNA
<213> ORGANISM: Artificial Sequence
<220> FEATURE:
<223> OTHER INFORMATION: Synthetic DNA

<400> SEQUENCE: 163
ggtttagcag gtaactgcag catcaatgtg tgcttaagca tgtgtacatt cctctcttac    60
ctataatggt acc                                                       73

<210> SEQ ID NO 164
<211> LENGTH: 58
<212> TYPE: DNA
<213> ORGANISM: Artificial Sequence
<220> FEATURE:
<223> OTHER INFORMATION: Synthetic DNA

<400> SEQUENCE: 164
cttctccttt actcatgtgt acattcctct cttacctata atggtaccgc tatcactt      58
```

METHOD FOR REGULATING EXPRESSION OF PROTEIN OF INTEREST IN BACILLUS SUBTILIS

TECHNICAL FIELD

The disclosure herein relates to a method for regulating expression of protein of interest in *Bacillus subtilis*, and belongs to the technical field of genetic engineering.

BACKGROUND

*Bacillus subtilis*, a model microorganism of gram-positive bacteria, is used in laboratory studies of sporulation mechanisms and metabolic regulation, and is widely distributed in nature, including soil surface, water environment and animal stomach. *Bacillus subtilis* is a non-pathogenic microorganism, is endotoxin-free and is generally accepted by the US Food and Drug Administration (FDA) as a safe (GRAS) food-grade microorganism. In addition, attributing to many advantages, including: rapid cell growth, short culture time, low culture requirements and strong ability to secrete proteins, *Bacillus subtilis* is widely used in industrial enzyme production and biosynthesis of high value-added products. However, the construction of regulatory element libraries in *Bacillus subtilis* still lags behind other important model organisms such as *Escherichia coli* and Saccharomyces cerevisiae.

To regulate gene expression in *Bacillus subtilis*, the currently used standard expression elements of *Bacillus subtilis* mainly include promoters, terminators, RBS sequence, SPACER and the like. In addition, an increasing number of genetic toolboxes related to *Bacillus subtilis* protein expression have been constructed. However, application of the current expression elements has their own disadvantages, including ineffective effects, high operating costs, and the like. Also, most of the standard elements focus on the regulation of transcription level, and have fewer translation level control tools and components, while the translation levels have a large impact on gene expression. Therefore, it is important to develop an easy-to-use expression regulation element in *Bacillus subtilis*.

SUMMARY

The first object of the present disclosure is to provide a method for regulating expression of protein of interest in *Bacillus subtilis*, which includes: modifying the N-terminal sequence of the protein of interest, and transferring the coding gene of the modified protein of interest into *Bacillus subtilis* for expression, wherein the N-terminal sequence is a sequence of the 1st to 15th amino acids of the N-terminal of the protein of interest or a nucleotide sequence coding the same, and the modifying method includes any one or more of the following:

(1) adding an N-terminal sequence element at the N-terminal of the protein of interest, wherein the N-terminal sequence element is an amino acid sequence coded by a specific nucleotide sequence, and the specific nucleotide sequence includes any one of SEQ ID NO.1-SEQ ID NO.109; or (2) listing serine (S), tryptophan (W), aspartic acid (D), cysteine (C), glycine (G), leucine (L), histidine (H) and arginine (R) in the N-terminal sequence of the proteins of interest as the first candidate sites; when the 2nd amino acid of the N-terminal is not asparagine (N), lysine (K) or glutamic acid (E), listing the 2nd site of the N-terminal as the second candidate site, and then replacing the first and the second candidate sites with any one of asparagine, lysine and glutamic acid, wherein during replacing, the following (a) and (b) are satisfied:

(a) when the previous amino acid or the latter amino acid of the first candidate sites or the second candidate site is any one of asparagine, lysine and glutamic acid, replacing the candidate site with the amino acid same as the previous amino acid or the latter amino acid; however, if after replacement, four or more consecutive amino acids consisting of any one or more of asparagine, lysine and glutamic acid are contained in seven amino acids from the first three to the last three from the candidate site, replacing the candidate site with glutamine (Q) or isoleucine (I);

(b) subject to priority to (a), the difference between any two of the number of candidate sites replaced with asparagine, the number of candidate sites replaced with lysine and the number of candidate sites replaced with glutamic acid being not exceeding 2; or (3) listing the sites of asparagine, lysine, glutamic acid and glutamine in the N-terminal sequences of the proteins of interest as the third candidate sites, and then, sequentially replacing the third candidate sites with serine, tryptophan, aspartic acid and cysteine; or (4) replacing the second, sixth and tenth amino acids of the N-terminal sequence with leucine.

In an embodiment of the present disclosure, the specific nucleotide sequences, SEQ ID NO.1-SEQ ID NO.109, are divided into four patterns according to regulatory functions:

1) growth-coupled pattern: the N-terminal sequence element regulating the protein of interest to be mainly expressed before a stationary phase, and the nucleotide sequence of the N-terminal sequence element being as shown in any one of SEQ ID NO.1-SEQ ID NO.15;

2) growth-delayed pattern: the N-terminal sequence element regulating the protein of interest to be mainly expressed at the end of a logarithmic growth phase and at the stationary phase; the nucleotide sequence of the growth-delayed pattern N-terminal sequence element being as shown in SEQ ID NO.16 or SEQ ID NO.17;

3) consistent expression pattern: the N-terminal sequence element regulating the protein of interest to be expressed throughout all phases of cell growth; the nucleotide sequence of the consistent expression pattern N-terminal sequence element being as shown in any one of SEQ ID NO.17-SEQ ID NO.102;

4) strongly inhibitory pattern: the N-terminal sequence element regulating the expression of the protein of interest to be strongly inhibited; the nucleotide sequence of the strongly inhibitory pattern N-terminal sequence element being as shown in any one of SEQ ID NO.103-SEQ ID NO.109.

In an embodiment of the present disclosure, the growth-coupled pattern N-terminal sequence element is used for regulating the protein of interest to be expressed before a stationary phase.

In an embodiment of the present disclosure, the growth-delayed pattern N-terminal sequence element is used for regulating the protein of interest to be expressed at the end of a logarithmic growth phase and at the stationary phase.

In an embodiment of the present disclosure, the consistent expression pattern N-terminal sequence element is used for regulating the protein of interest to be expressed throughout all phases of cell growth.

In an embodiment of the present disclosure, the strongly inhibitory pattern N-terminal sequence element is used for inhibiting the expression of the protein of interest.

In an embodiment of the present disclosure, the N-terminal sequence element of the modified protein of interest in (2) comprises SEQ ID NO.110-SEQ ID NO.123.

In an embodiment of the present disclosure, the N-terminal sequence element of the modified protein of interest in (3) comprises SEQ ID NO.124-SEQ ID NO.130.

In an embodiment of the present disclosure, the N-terminal sequence element of the modified protein of interest in (4) comprises SEQ ID NO.131-SEQ ID NO.137.

In an embodiment of the present disclosure, the *Bacillus subtilis* comprises *Bacillus subtilis* 168, *Bacillus subtilis* WB400, *Bacillus subtilis* WB600 and *Bacillus subtilis* WB800.

In an embodiment of the present disclosure, the expression vector comprises pP43NMK.

In an embodiment of the present disclosure, the protein of interest comprises enzyme protein and non-enzymatic protein.

In an embodiment of the present disclosure, after replacement in (2) the asparagine uses the codon AAC or AAT, the lysine uses the codon AAA, the glutamic acid uses the codon GAA, and the glutamine uses the codon CAA.

In an embodiment of the present disclosure, after replacement in (3), the serine uses the codon TCC or TCT, the tryptophan uses the codon TGG, the aspartic acid uses the codon GAT, and the cysteine uses the codon TGT.

In an embodiment of the present disclosure, after replacement in (4), the leucine uses the codon CTT, TTG or TTA.

In an embodiment of the present disclosure, (2) is used for improving the expression level of *Bacillus subtilis* protein.

In an embodiment of the present disclosure, (3) is used for reducing the expression level of *Bacillus subtilis* protein.

In an embodiment of the present disclosure, (4) is used for coupling *Bacillus subtilis* protein expression with strain growth.

The second object of the present disclosure is to provide recombinant protein modified by the above methods, the recombinant protein comprises the amino acid sequence as shown in any one of SEQ ID NO.109-SEQ ID NO.137, or, the gene coding the recombinant protein comprises the nucleotide sequence as shown in any one of SEQ ID NO.1-SEQ ID NO.109.

The third object of the present disclosure is to provide cells or vectors expressing the recombinant protein.

Advantages and Effects of the Present Disclosure

The present disclosure uses *Bacillus subtilis* as an expression host, by adding the N-terminal nucleotide sequence coding the first 15 amino acids of the endogenous protein before the coding gene of the protein of interest or modifying the original N-terminal sequence, and performing free expression in plasmids, expression of the protein of interest in *Bacillus subtilis* is regulated, and even the expression difference in different growth phases and the expression level are regulated. The effects which can be achieved are as follows:

In the modification method (1), an N-terminal sequence which increases the expression level of the protein is added to the N-terminal of the protein of interest; when the added N-terminal sequence is SEQ ID NO.18, fermentation of recombinant bacteria for 4 h can increase the average fluorescent intensity from about 5159 to 35837, and fermentation for 20 h can increase the fluorescent intensity from about 48181 to 138986, which respectively increase to 6.95 times and 2.88 times of that of the control. An N-terminal sequence which reduces the expression level of protein is added to the N-terminal sequence of the protein of interest; when the N-terminal sequence is SEQ ID NO.107, fermentation for 4 h can reduce the average fluorescent intensity from about 5159 to 55, and fermentation for 20 h can reduce the fluorescent intensity from about 48181 to 1125, which respectively reduce to 0.011 time and 0.023 time of that of the control.

In the modification method (2), taking an original N-terminal sequence MARYTGPSWKLSRRL (i.e. SEQ ID NO.149) as an example, after artificial modification, SEQ ID NO.121 is obtained, and after fermentation for 4 h, the relative fluorescent intensity increases from 55 to 21948.3, which is 397 times of the original.

In the modification method (3), taking an original N-terminal sequence MRINHNIAALNTLNR (i.e. SEQ ID NO.140) as an example, after artificial modification, SEQ ID NO.127 is obtained, and after fermentation for 4 h, the relative fluorescent intensity decreases from 22320.6 to 432.9, which is 1.94% of the original.

In the modification method (4), using an original N-terminal sequence SEQ ID NO.33 as an example, after artificial modification, SEQ ID NO.132 is obtained, which enables the protein of interest to be expressed before a stationary phase of *Bacillus subtilis* growth, and after cell growth ends, the relative fluorescent intensity remains relatively balanced.

Figure 1:
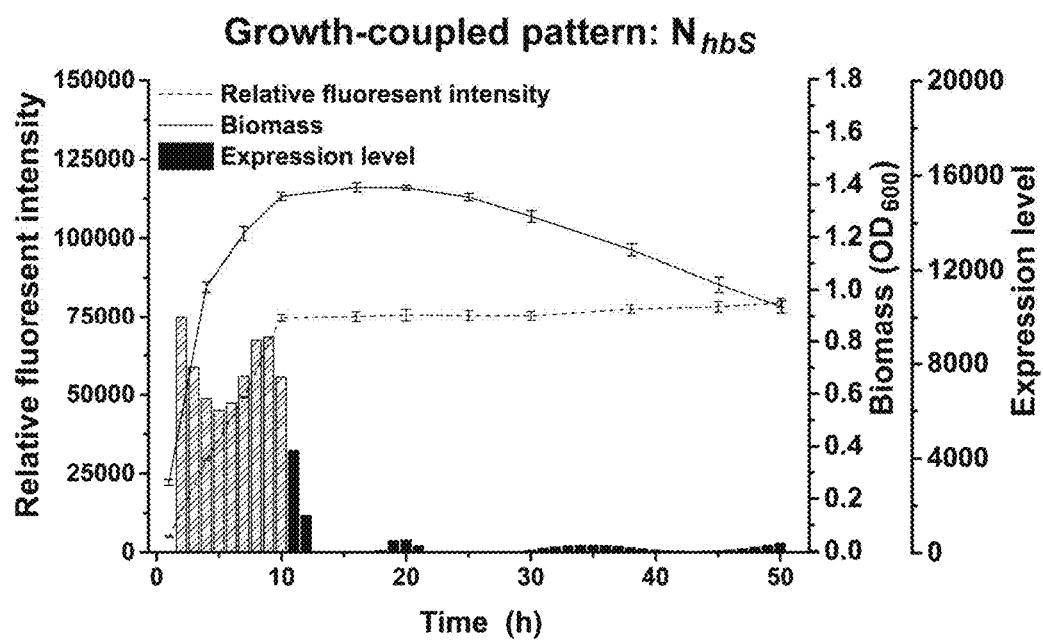
FIG. 1 shows the effects of addition of Nubs growth-coupled pattern nucleotide sequence as shown in SEQ ID NO.1 to N-terminal on protein expression.

DETAILED DESCRIPTION (1) Recombinant *Bacillus subtilis* seed culture and fermentation Medium (g/L): tryptone 10, yeast powder 5, NaCl 10.

Culture conditions: transferring seeds cultured at 37° C., 200 rpm for 10 h to the fermentation medium according to an inoculum size of 10% (v/v), and culturing the seeds at 37° C., 200 rpm for 20 h.

(2) Method for determining the expression level of green fluorescent protein

Adding 200 μL of diluted fermentation broth to each well in a 96-well plate, and using a Cytation 3 cell imaging microplate reader (Berton Instruments, Inc., USA), specifically, excitation wavelength: 488 nm, emission wavelength: 523 nm, and gain: 60.

Example 1

Effects of Addition of Nucleotide Sequences as Shown in SEQ ID NO.1-SEQ ID NO.109 to N-Terminal on Expression of Green Fluorescent Protein in Engineering Bacteria 1. Construction of Recombinant Plasmid The composition of recombinant plasmid is that the nucleotide sequence to be added and the green fluorescent protein (GFP) gene are sequentially inserted after the P43 promoter of Pp43NMK plasmid.

To introduce the nucleotide sequence to be added after the P43 promoter, primers rh_CspD-0.75k_p43NMK-GFP_F: 5'-TGGTTCAACGAAAAAGGATTCATGAGTAAAG-GAGAAGAACTTTTCACTGGAGTTGTCCCA-3' (i e SEQ ID NO. 152), and rh_CspD-0.75k_p43NMK-GFP_R: 5'-TACGCCAAGCTTTCATCACTATTTGTATAGTT-CATCCATGCCATGTGTAATCCCAGCAG-3' (i e SEQ ID NO.153) were designed, *Escherichia coli* containing the green fluorescent protein (GFP, GenBank: AF324408.1) gene was used as a template, and a green fluorescent protein fragment was obtained by colony PCR.

Primers fx_CspD-6.7k_p43NMK-GFP_F: 5'-AGTGAT-GAAAGCTTGGCGTAATCATGGTCATAGCTGTTT-3' (i e SEQ ID NO.154), and fx_CspD-6.7k_p43NMK-GFP_R: 5'-CCTTTTTCGTTGTTGAACCATTTTACTT-TACCGTTTTGCATGTGTACATTCCTCTCTTACC-TATAATGGTACCGCTATCACTT-3' (i e SEQ ID NO.155) were designed. Plasmid pP43NMK was used as a template and a plasmid fragment was obtained by reverse amplification by PCR. Finally, the recombinant plasmid was constructed by Gibson Assembly Clonging Kit (New England Biolabs), and it was verified that the construction of the recombinant pP43NMK-TufAN-GFP plasmid is successful by sequencing.

2. Construction of Recombinant pP43NMK-CspDN-GFP Plasmid *Bacillus Subtilis*

The constructed pP43NMK-CspDN-GFP plasmid was transformed into a wild type strain of *Bacillus subtilis* 168. Primers yz_zong-p43NMK_F: 5'-TTCTTGCT-GAGTCTGGCTTTCG-3' (i e SEQ ID NO.156) and yz_zong-p43NMK_R: 5'-CGGCTCGTATGTTGTGTG-GAAT-3' (i e SEQ ID NO.157) was used to select transformants for colony PCR, and it was verified that the construction of the recombinant *Bacillus subtilis* is successful when a 1.8 kb band appeared.

3. Expression of Green Fluorescent Protein in Engineering Bacteria After Addition of Nucleotide Sequences as Shown in SEQ ID NO.1-SEQ ID NO.109 to N-Terminal Seeds of the successfully constructed recombinant *Bacillus subtilis* cultured at 37° C., 750 rpm in a 700 μL LB medium and in a 96-well plate for 9 h were transferred to a 190 μL LB medium according to an inoculum size of 5% (v/v), and cultured at 37° C., 750 rpm for 4 h and 20 h. Under the same conditions, if only expressed by pP43NMK, with no regulatory N-terminal nucleotide sequence added, the average fluorescent intensity in the final fermentation broth was about 5159 measured after 4 h, and about 48181 after 20 h. While after the N-terminal sequence of GLNA protein was added, the average fluorescent intensity was 20912.3 measured after 4 h, and the average fluorescent intensity was 105441.4 after 20 h, which were respectively 4 times and 2 times of that of the control.

The effects of addition of the nucleotide sequences as shown in SEQ ID NO.1-SEQ ID NO.109 to the N-terminal on expression of green fluorescent protein in engineering bacteria is summarized as follows:

(1) The effects of regulating protein expression: the expression level of protein is characterized by fluorescent intensity. According to the fluorescent intensity determination method described herein, the range of expression level of protein regulated by the N-terminal sequence element spans four orders of magnitude. The expression level of protein can be increased by about 7 times compared to the control. In the nucleotide sequence which increases the protein expression level, when the sequence added to the N-terminal is the N-terminal nucleotide sequence (i.e. SEQ ID NO.18) coding the first 15 amino acids of YdbP protein, and the fermentation time is 4 h, the average fluorescent intensity is increased from about 5159 to 35,837, and when the fermentation time is 20 h, the fluorescent intensity is increased from about 48181 to 138986, which are respectively increased to 6.95 times and 2.88 times of that of the control. In the N-terminal nucleotide sequence which decreases the protein expression level, when the sequence added to the N-terminal is the N-terminal nucleotide sequence (i.e. SEQ ID NO.107) coding the first 15 amino acids of RspD protein, and the fermentation time is 4 h, the average fluorescent intensity is decreased from about 5159 to 55, and when the fermentation time is 20 h, the fluorescent intensity is decreased from about 48181 to 1125, which are respectively decreased to 0.011 time and 0.023 time of that of the control. The regulation effects of addition of 109 different specific nucleotide sequences on the expression of green fluorescent protein are shown in Tables 1-4.

Figure 2:
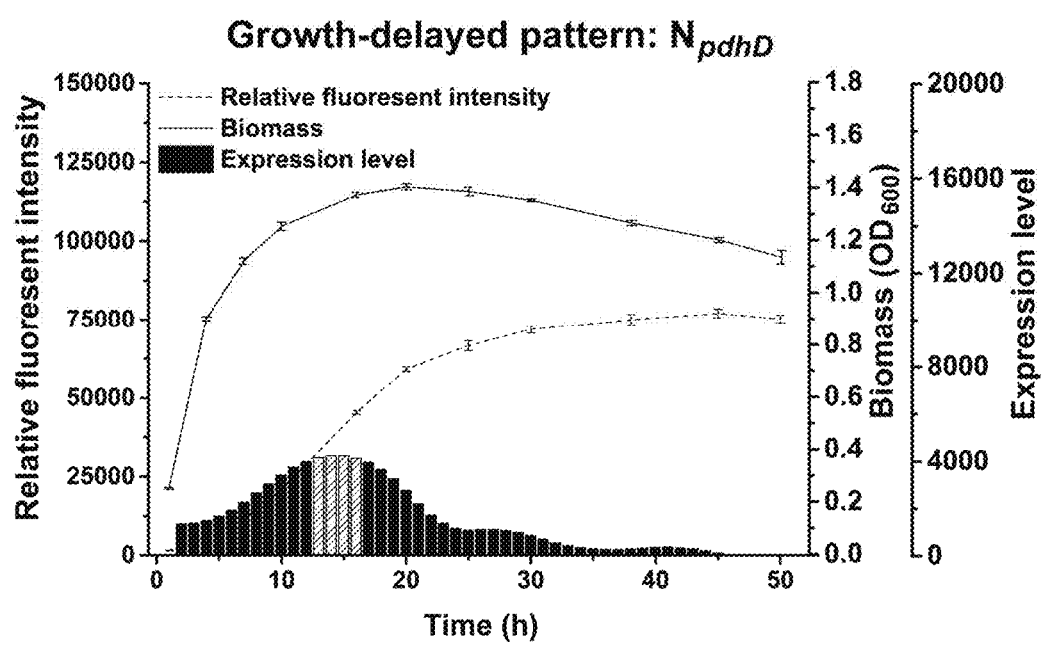
FIG. 2 shows the effects of addition of $N_p$dhD growth-delayed pattern nucleotide sequence as shown in SEQ ID NO.17 to N-terminal on protein expression.
Figure 3:
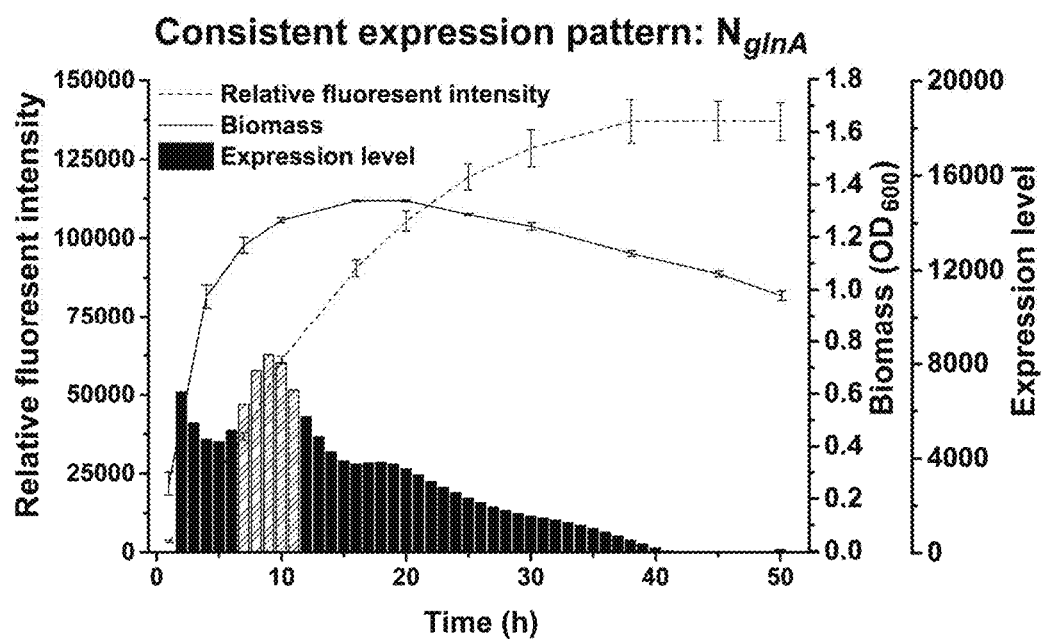
FIG. 3 shows the effects of addition of $N_{glnA}$ consistent expression pattern nucleotide sequence as shown in SEQ ID NO.24 to N-terminal on protein expression.
Figure 4:
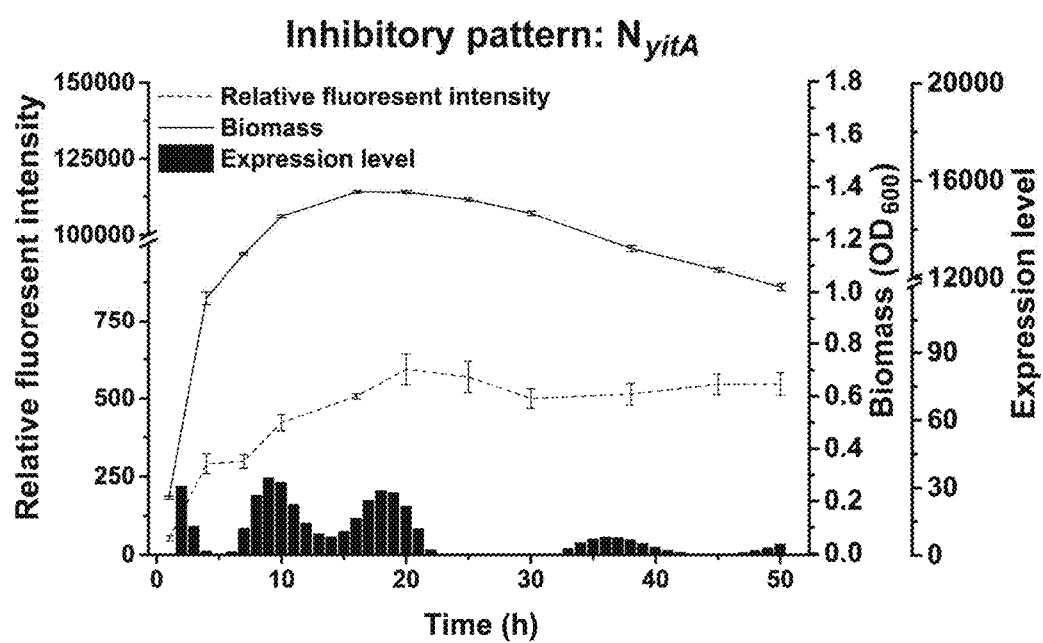
FIG. 4 shows the effects of addition of $N_{yitA}$ inhibitory pattern nucleotide sequence as shown in SEQ ID NO.104 to N-terminal on protein expression.

(2) The effects of regulating the difference in protein expression in different growth phases: the expression level of protein is characterized by fluorescent intensity. According to the fluorescent intensity determination method described herein, the N-terminal sequence element can regulate differential expression of the protein of interest in different growth phases of *Bacillus subtilis*, and are divided into growth-coupled pattern, growth-delayed pattern, consistent expression pattern and inhibitory pattern. In the growth-coupled pattern, using the N-terminal sequence of Hbs protein (i.e. SEQ ID NO.1) as an example, the protein expression is mainly concentrated within 10 h, i.e., before the end of the growth logarithm (FIG. 1); in the growth-delayed pattern, using the N-terminal sequence of PdhD (i.e. SEQ ID NO.17) protein as an example, the protein expression is mainly concentrated within about 15 h, i.e., the end of the growth logarithm (FIG. 2); in the consistent expression pattern, using the N-terminal nucleotide sequence of GlnA protein (i.e. SEQ ID NO.24) as an example, the protein expression is throughout all phases of the whole growth period (FIG. 3); in the strongly inhibitory pattern, using the N-terminal sequence of YitA protein (i.e. SEQ ID NO.104) as an example, the protein expression is strongly inhibited all the time (FIG. 4).

TABLE 1

Effects of growth-coupled pattern N-terminal nucleotide sequence on protein expression

| | Fermentation time | | | | | |
|---|---|---|---|---|---|---|
| | 4 h | | | 20 h | | |
| N-terminal sequence number | Average fluorescent intensity | Error | Gain | Average fluorescent intensity | Error | Gain |
| SEQ ID NO. 1 | 29414.20 | 346.01 | 5.70 | 75686.25 | 1841.23 | 1.57 |
| SEQ ID NO. 2 | 19751.75 | 330.34 | 3.83 | 38773.67 | 856.29 | 0.80 |
| SEQ ID NO. 3 | 16854.80 | 402.15 | 3.27 | 38603.00 | 1873.35 | 0.80 |
| SEQ ID NO. 4 | 14383.60 | 439.30 | 2.79 | 33570.60 | 681.03 | 0.70 |
| SEQ ID NO. 5 | 13959.00 | 73.27 | 2.71 | 34834.00 | 1057.41 | 0.72 |
| SEQ ID NO. 6 | 10603.40 | 226.51 | 2.06 | 19196.25 | 825.25 | 0.40 |
| SEQ ID NO. 7 | 10244.80 | 152.32 | 1.99 | 13512.96 | 415.43 | 0.28 |
| SEQ ID NO. 8 | 10085.00 | 278.36 | 1.95 | 29682.67 | 678.99 | 0.62 |
| SEQ ID NO. 9 | 7655.60 | 390.59 | 1.48 | 14547.20 | 817.08 | 0.30 |
| SEQ ID NO. 10 | 7153.20 | 136.10 | 1.39 | 17905.20 | 1407.45 | 0.37 |
| SEQ ID NO. 11 | 7045.50 | 589.50 | 1.37 | 17436.50 | 55.50 | 0.36 |
| SEQ ID NO. 12 | 6954.40 | 324.35 | 1.35 | 19980.80 | 2406.37 | 0.41 |
| SEQ ID NO. 13 | 5659.33 | 54.06 | 1.10 | 17053.67 | 1177.22 | 0.35 |
| SEQ ID NO. 14 | 4909.60 | 207.80 | 0.95 | 5833.20 | 428.00 | 0.12 |
| SEQ ID NO. 15 | 3559.20 | 30.79 | 0.69 | 6232.00 | 436.98 | 0.13 |

TABLE 2

Effects of growth-delayed pattern N-terminal nucleotide sequence on protein expression

| | Fermentation time | | | | | |
|---|---|---|---|---|---|---|
| | 4 h | | | 20 h | | |
| N-terminal sequence number | Average fluorescent intensity | Error | Gain | Average fluorescent intensity | Error | Gain |
| SEQ ID NO. 16 | 6531.00 | 310.18 | 1.27 | 66030.47 | 804.18 | 1.37 |
| SEQ ID NO. 17 | 5384.40 | 66.74 | 1.04 | 59055.40 | 773.50 | 1.23 |

TABLE 3

Effects of persistent expression pattern N-terminal nucleotide sequence on protein expression

| | Fermentation time | | | | | |
|---|---|---|---|---|---|---|
| | 4 h | | | 20 h | | |
| N-terminal sequence number | Average fluorescent intensity | Error | Gain | Average fluorescent intensity | Error | Gain |
| SEQ ID NO. 18 | 35836.80 | 337.00 | 6.95 | 138985.86 | 353.10 | 2.88 |
| SEQ ID NO. 19 | 23509.80 | 173.96 | 4.56 | 75249.75 | 1820.29 | 1.56 |
| SEQ ID NO. 20 | 23045.80 | 324.31 | 4.47 | 89647.50 | 511.50 | 1.86 |
| SEQ ID NO. 21 | 22951.60 | 348.70 | 4.45 | 83260.30 | 871.40 | 1.73 |
| SEQ ID NO. 22 | 21945.80 | 142.44 | 4.25 | 67284.80 | 692.00 | 1.40 |
| SEQ ID NO. 23 | 21802.13 | 289.37 | 4.23 | 114839.71 | 878.13 | 2.38 |
| SEQ ID NO. 24 | 20912.30 | 769.39 | 4.05 | 105441.36 | 3150.72 | 2.19 |
| SEQ ID NO. 25 | 20797.80 | 481.64 | 4.03 | 68119.80 | 181.00 | 1.41 |
| SEQ ID NO. 26 | 20088.00 | 331.23 | 3.89 | 96630.34 | 3163.70 | 2.01 |
| SEQ ID NO. 27 | 17889.05 | 318.81 | 3.47 | 82486.00 | 1029.00 | 1.71 |
| SEQ ID NO. 28 | 17256.20 | 399.50 | 3.34 | 111246.91 | 1466.33 | 2.31 |
| SEQ ID NO. 29 | 15324.89 | 526.42 | 2.97 | 82620.80 | 2808.92 | 1.71 |
| SEQ ID NO. 30 | 14258.40 | 335.07 | 2.76 | 84556.40 | 1833.33 | 1.75 |

TABLE 3-continued

Effects of persistent expression pattern N-terminal nucleotide sequence on protein expression

| | Fermentation time | | | | | |
|---|---|---|---|---|---|---|
| | 4 h | | | 20 h | | |
| N-terminal sequence number | Average fluorescent intensity | Error | Gain | Average fluorescent intensity | Error | Gain |
| SEQ ID NO. 31 | 13612.60 | 147.36 | 2.64 | 54321.00 | 1047.92 | 1.13 |
| SEQ ID NO. 32 | 13603.20 | 253.72 | 2.64 | 47903.20 | 3804.04 | 0.99 |
| SEQ ID NO. 33 | 13125.60 | 389.66 | 2.54 | 48212.50 | 83.50 | 1.00 |
| SEQ ID NO. 34 | 12150.20 | 376.38 | 2.36 | 56608.67 | 846.96 | 1.17 |
| SEQ ID NO. 35 | 11568.20 | 136.24 | 2.24 | 57555.50 | 1533.43 | 1.19 |
| SEQ ID NO. 36 | 10566.00 | 228.69 | 2.05 | 46124.75 | 1728.34 | 0.96 |
| SEQ ID NO. 37 | 10072.44 | 333.26 | 1.95 | 31078.27 | 515.74 | 0.65 |
| SEQ ID NO. 38 | 9963.20 | 104.03 | 1.93 | 48847.30 | 581.14 | 1.01 |
| SEQ ID NO. 39 | 9869.00 | 163.03 | 1.91 | 45881.00 | 710.48 | 0.95 |
| SEQ ID NO. 40 | 9797.00 | 251.75 | 1.90 | 53319.00 | 239.00 | 1.11 |
| SEQ ID NO. 41 | 9162.82 | 108.49 | 1.78 | 18175.10 | 1096.50 | 0.38 |
| SEQ ID NO. 42 | 9024.38 | 111.53 | 1.75 | 22141.35 | 630.73 | 0.46 |
| SEQ ID NO. 43 | 8809.52 | 82.33 | 1.71 | 15728.10 | 748.38 | 0.33 |
| SEQ ID NO. 44 | 7788.86 | 44.34 | 1.51 | 22172.27 | 639.97 | 0.46 |
| SEQ ID NO. 45 | 7146.97 | 497.00 | 1.39 | 15131.30 | 819.34 | 0.31 |
| SEQ ID NO. 46 | 6699.40 | 107.45 | 1.30 | 18106.50 | 689.82 | 0.38 |
| SEQ ID NO. 47 | 6474.20 | 78.58 | 1.25 | 26126.00 | 2018.29 | 0.54 |
| SEQ ID NO. 48 | 6432.00 | 358.36 | 1.25 | 23656.75 | 876.07 | 0.49 |
| SEQ ID NO. 49 | 6360.55 | 176.32 | 1.23 | 22855.40 | 1123.12 | 0.47 |
| SEQ ID NO. 50 | 5986.60 | 143.00 | 1.16 | 16732.25 | 388.09 | 0.35 |
| SEQ ID NO. 51 | 5914.20 | 215.96 | 1.15 | 19270.13 | 269.82 | 0.40 |
| SEQ ID NO. 52 | 5615.46 | 151.52 | 1.09 | 28803.20 | 1405.52 | 0.60 |
| SEQ ID NO. 53 | 5391.60 | 177.68 | 1.05 | 29367.00 | 69.00 | 0.61 |
| SEQ ID NO. 54 | 5186.80 | 164.15 | 1.01 | 21933.47 | 1350.77 | 0.46 |
| SEQ ID NO. 55 | 4905.60 | 253.58 | 0.95 | 28629.67 | 522.02 | 0.59 |
| SEQ ID NO. 56 | 4836.97 | 69.30 | 0.94 | 11572.60 | 703.06 | 0.24 |
| SEQ ID NO. 57 | 4690.37 | 183.49 | 0.91 | 13302.60 | 582.46 | 0.28 |
| SEQ ID NO. 58 | 4485.46 | 252.50 | 0.87 | 11861.60 | 501.86 | 0.25 |
| SEQ ID NO. 59 | 4447.20 | 295.91 | 0.86 | 16007.50 | 451.77 | 0.33 |
| SEQ ID NO. 60 | 4438.10 | 167.55 | 0.86 | 8401.60 | 564.91 | 0.17 |
| SEQ ID NO. 61 | 3894.00 | 103.93 | 0.75 | 20521.60 | 886.87 | 0.43 |
| SEQ ID NO. 62 | 3659.42 | 48.73 | 0.71 | 7100.00 | 414.57 | 0.15 |
| SEQ ID NO. 63 | 3364.40 | 91.35 | 0.65 | 8628.20 | 643.51 | 0.18 |
| SEQ ID NO. 64 | 3259.99 | 13.18 | 0.63 | 14573.35 | 662.25 | 0.30 |
| SEQ ID NO. 65 | 3026.00 | 101.30 | 0.59 | 12411.20 | 518.47 | 0.26 |
| SEQ ID NO. 66 | 2825.40 | 66.11 | 0.55 | 4809.20 | 201.14 | 0.10 |
| SEQ ID NO. 67 | 2792.20 | 31.94 | 0.54 | 13054.20 | 586.12 | 0.27 |
| SEQ ID NO. 68 | 2791.20 | 100.59 | 0.54 | 8027.40 | 475.02 | 0.17 |
| SEQ ID NO. 69 | 2722.00 | 42.99 | 0.53 | 7114.60 | 526.61 | 0.15 |
| SEQ ID NO. 70 | 2621.60 | 82.95 | 0.51 | 8051.20 | 791.16 | 0.17 |
| SEQ ID NO. 71 | 2602.40 | 84.76 | 0.50 | 3911.20 | 350.91 | 0.08 |
| SEQ ID NO. 72 | 2503.07 | 19.12 | 0.49 | 5894.27 | 131.82 | 0.12 |
| SEQ ID NO. 73 | 2422.00 | 111.74 | 0.47 | 8996.25 | 164.41 | 0.19 |
| SEQ ID NO. 74 | 2339.99 | 101.48 | 0.45 | 5425.40 | 448.66 | 0.11 |
| SEQ ID NO. 75 | 2323.00 | 65.08 | 0.45 | 8277.40 | 548.11 | 0.17 |
| SEQ ID NO. 76 | 2260.00 | 209.63 | 0.44 | 9925.33 | 414.96 | 0.21 |
| SEQ ID NO. 77 | 2128.00 | 86.23 | 0.41 | 7977.80 | 238.28 | 0.17 |
| SEQ ID NO. 78 | 2015.27 | 98.89 | 0.39 | 4215.20 | 301.67 | 0.09 |
| SEQ ID NO. 79 | 1943.20 | 150.95 | 0.38 | 6817.75 | 221.47 | 0.14 |
| SEQ ID NO. 80 | 1909.00 | 25.65 | 0.37 | 8892.40 | 376.89 | 0.18 |
| SEQ ID NO. 81 | 1852.80 | 23.86 | 0.36 | 7207.60 | 276.46 | 0.15 |
| SEQ ID NO. 82 | 1823.40 | 89.14 | 0.35 | 6360.80 | 496.35 | 0.13 |
| SEQ ID NO. 83 | 1749.40 | 75.94 | 0.34 | 6651.75 | 282.99 | 0.14 |
| SEQ ID NO. 84 | 1691.20 | 81.25 | 0.33 | 3745.25 | 318.03 | 0.08 |
| SEQ ID NO. 85 | 1389.00 | 65.97 | 0.27 | 9258.20 | 104.10 | 0.19 |
| SEQ ID NO. 86 | 1188.00 | 56.33 | 0.23 | 8448.04 | 101.37 | 0.18 |
| SEQ ID NO. 87 | 1085.80 | 38.30 | 0.21 | 4214.40 | 236.05 | 0.09 |
| SEQ ID NO. 88 | 1056.40 | 24.02 | 0.20 | 3152.40 | 18.25 | 0.07 |
| SEQ ID NO. 89 | 878.67 | 73.91 | 0.17 | 2963.80 | 111.71 | 0.06 |
| SEQ ID NO. 90 | 400.55 | 43.38 | 0.08 | 3622.40 | 295.72 | 0.08 |
| SEQ ID NO. 91 | 31097.37 | 389.49 | 6.03 | 7334.80 | 129.16 | 2.75 |
| SEQ ID NO. 92 | 20571.67 | 335.67 | 3.99 | 5286.20 | 140.43 | 1.98 |
| SEQ ID NO. 93 | 29874.33 | 505.80 | 5.79 | 7127.00 | 69.77 | 2.67 |
| SEQ ID NO. 94 | 15592.69 | 463.03 | 3.02 | 3875.40 | 31.53 | 1.45 |
| SEQ ID NO. 95 | 26928.35 | 666.94 | 5.22 | 6938.80 | 69.44 | 2.60 |
| SEQ ID NO. 96 | 30069.00 | 310.65 | 5.83 | 8549.20 | 130.19 | 3.20 |
| SEQ ID NO. 97 | 16593.99 | 299.46 | 3.22 | 2699.20 | 53.34 | 1.01 |

TABLE 3-continued

Effects of persistent expression pattern N-terminal nucleotide sequence on protein expression

| N-terminal sequence number | Fermentation time | | | | | |
|---|---|---|---|---|---|---|
| | 4 h | | | 20 h | | |
| | Average fluorescent intensity | Error | Gain | Average fluorescent intensity | Error | Gain |
| SEQ ID NO. 98 | 34317.64 | 598.92 | 6.65 | 8460.80 | 224.50 | 3.17 |
| SEQ ID NO. 99 | 33091.00 | 969.69 | 6.41 | 9134.60 | 272.43 | 3.42 |
| SEQ ID NO. 100 | 31810.76 | 1080.67 | 6.17 | 5558.40 | 250.04 | 2.08 |
| SEQ ID NO. 101 | 26750.70 | 915.80 | 5.19 | 6420.60 | 168.96 | 2.40 |
| SEQ ID NO. 102 | 33829.93 | 290.91 | 6.56 | 8101.20 | 229.42 | 3.03 |

TABLE 4

Effects of inhibitory pattern N-terminal nucleotide sequences on protein expression

| N-terminal sequence number | Fermentation time | | | | | |
|---|---|---|---|---|---|---|
| | 4 h | | | 20 h | | |
| | Average fluorescent intensity | Error | Gain | Average fluorescent intensity | Error | Gain |
| SEQ ID NO. 103 | 415.60 | 30.37 | 0.08 | 1228.20 | 56.40 | 0.03 |
| SEQ ID NO. 104 | 281.80 | 31.58 | 0.05 | 990.20 | 49.25 | 0.02 |
| SEQ ID NO. 105 | 167.16 | 17.95 | 0.03 | 671.00 | 72.92 | 0.01 |
| SEQ ID NO. 106 | 106.97 | 22.57 | 0.02 | 1203.60 | 173.20 | 0.02 |
| SEQ ID NO. 107 | 55.27 | 8.07 | 0.01 | 1125.00 | 87.28 | 0.02 |
| SEQ ID NO. 108 | 48.10 | 13.22 | 0.01 | 0.00 | 13.54 | 0.00 |
| SEQ ID NO. 109 | 0.00 | 14.14 | 0.00 | 178.60 | 71.78 | 0.00 |

Example 2

Effects of Modification of N-Terminal Sequence on the Expression of Green Fluorescent Protein in Engineering Bacteria 1. Construction of Recombinant Plasmid The composition of the recombinant plasmid is that the N-terminal sequence element and the green fluorescent protein (GFP) gene are sequentially inserted after the P43 promoter of Pp43NMK plasmid. To introduce the N-terminal sequence element after the P43 promoter, primers rh_sigw-0.75k_p43NMK-GFP_F: 5'-GATGAT-TAAAAAAAACATTAAACAAAACAAAAAAAACAT-GAGTAAAGGAGAAGAACTTTTCACTGGAG-3' (i.e. SEQ ID NO.158), and rh_sigw-0.75k_p43NMK-GFP_R: 5'-AGTGATGAAAGCTTGGCGTAATCATGGTCAT-AGCTGTTT-3' (i.e. SEQ ID NO.152) were designed. Escherichia coli containing the green fluorescent protein (GFP, GenBank: AF324408.1) gene was used as a template, and a green fluorescent protein fragment was obtained by colony PCR. Primers fx_sigw-6.7k_p43NMK-GFP_F: 5'-TTACACATGGCATGGATGAACTATACAAATAGT-GATGAAAGCTTGGCGTAATCATGGTCATAGCTG-3' (i.e. SEQ ID NO.159), and fx_sigw-6.7k_p43NMK-GFP_R: 5'-TGTTTAATGTTTTTTTTAATCATCATTTC-CATGTGTACATTCCTCTCTTACCTATAATGGTACC-3' (i.e. SEQ ID NO.160) were designed.

Plasmid pP43NMK was used as a template and a plasmid fragment was obtained by reverse amplification by PCR. Finally, the recombinant plasmid was constructed by Gibson Assembly Clonging Kit (New England Biolabs), and it was verified that the construction of the recombinant pP43NMK-TufAN-GFP plasmid was successful by sequencing.

2. Construction of Recombinant pP43NMK-sigw-GFP Plasmid Bacillus Subtilis

The constructed pP43NMK-GLNA-GFP plasmid was transformed into a wild type strain of Bacillus subtilis 168. Primers yz_zong-p43NMK_F: 5'-TTCTTGCT-GAGTCTGGCTTTCG-3' (i.e. SEQ ID NO.156) and yz_zong-p43NMK_R: 5'-CGGCTCGTATGTTGTGTG-GAAT-3' (i.e. SEQ ID NO.157) were used to select transformants for colony PCR, and it was verified that the construction of the recombinant Bacillus subtilis is successful when a 1.8 kb band appeared.

3. Expression of Green Fluorescent Protein in Engineering Bacteria After Addition of Artificially Designed N-Terminal Sequence Element A recombinant Bacillus subtilis seed solution cultured at 37° C., 750 rpm in a 700 μL LB medium and in a 96-well deep-well plate for 9 h was transferred to a 190 μL LB medium according to an inoculum size of 5% (v/v), and the seed solution was cultured at 37° C., 750 rpm for 4 h to obtain a recombinant Bacillus subtilis culture solution sample. Under the same conditions, after the recombinant Bacillus subtilis with addition of the original N-terminal sequence element (i e SEQ ID NO.139) was fermented for 4 h, the average fluorescent intensity measured in the fermentation broth was about 22716. While after the artificially designed N-terminal sequence element (i e SEQ ID NO.111) was added, the average fluorescent intensity of the culture solution was 34819 after the recombinant Bacillus subtilis is cultured for 4 hours.

The effects of 14 different original N-terminal sequence elements on the expression level of green fluorescent protein after artificial modification is shown in Table 5.

TABLE 5

Effects of 21 artificially designed N-terminal sequence elements on protein expression

| Original N-terminal sequence | Relative fluorescent intensity | Increase of expression level by modification | Relative fluorescent intensity | Gain | Decrease of expression level by modification | Relative fluorescent intensity | Gain |
|---|---|---|---|---|---|---|---|
| SEQ ID NO. 138 | 32608 | SEQ ID NO. 110 | 42986 | 1.32 | SEQ ID NO. 124 | 5310 | 0.16 |
| SEQ ID NO. 139 | 22716 | SEQ ID NO. 111 | 34819 | 1.53 | SEQ ID NO. 125 | 903 | 0.04 |
| SEQ ID NO. 140 | 22321 | SEQ ID NO. 112 | 40543 | 1.82 | SEQ ID NO. 126 | 433 | 0.02 |
| SEQ ID NO. 141 | 22224 | SEQ ID NO. 113 | 37861 | 1.70 | SEQ ID NO. 127 | 1314 | 0.06 |
| SEQ ID NO. 142 | 20756 | SEQ ID NO. 114 | 27496 | 1.32 | SEQ ID NO. 128 | 1727 | 0.08 |
| SEQ ID NO. 143 | 16895 | SEQ ID NO. 115 | 32362 | 1.92 | SEQ ID NO. 129 | 650 | 0.04 |
| SEQ ID NO. 144 | 20034 | SEQ ID NO. 116 | 37069 | 1.85 | SEQ ID NO. 130 | 5518 | 0.28 |
| SEQ ID NO. 145 | 416 | SEQ ID NO. 117 | 5171 | 12.44 | | | |
| SEQ ID NO. 146 | 282 | SEQ ID NO. 118 | 7712 | 27.37 | | | |
| SEQ ID NO. 147 | 167 | SEQ ID NO. 119 | 7270 | 43.49 | | | |
| SEQ ID NO. 148 | 107 | SEQ ID NO. 120 | 10280 | 96.11 | | | |
| SEQ ID NO. 149 | 55 | SEQ ID NO. 121 | 21948 | 397.10 | | | |
| SEQ ID NO. 150 | 48 | SEQ ID NO. 122 | 8123 | 168.86 | | | |
| SEQ ID NO. 151 | 0 | SEQ ID NO. 123 | 7074 | / | | | |

Example 3

Effects 2 of Addition of Artificially Designed N-Terminal Sequence Elements on Expression of Green Fluorescent Protein in Engineering Bacteria 1. Construction of Recombinant Plasmid The composition of the recombinant plasmid is that the N-terminal sequence element and the green fluorescent protein (GFP) gene are sequentially inserted after the P43 promoter of Pp43NMK plasmid. To introduce the N-terminal sequence element after the P43 promoter, primers rh_NO132-0.75k_p43NMK-GFP_F: 5'-CTGCAGT-TACCTGCTAAACCAGATATGAGTAAAGGAGAA-GAACTTTTCACTGGAG-3' (i.e. SEQ ID NO.161), and rh_NO132-0.75k_p43NMK-GFP_R: 5'-CGATATCTTCT-CTAGTGTACTTTGCCATGTGTACATTCCTCTCT-TACCTATAATGGTACCGCTATCACTT-3' (i.e. SEQ ID NO.162) were designed, Escherichia coli containing the green fluorescent protein (GFP, GenBank: AF324408.1) gene was used as a template, and a green fluorescent protein fragment was obtained by colony PCR. Primers fx_NO132-6.7k_p43NMK-GFP_F: 5'-AGTGAT-GAAAGCTTGGCGTAATCATGGTCATAGCTGTTT-3' (i.e. SEQ ID NO.152), and fx_NO132-6.7k_p43NMK-GFP_R: 5'-GGTTTAGCAGGTAACTGCAGCAT-CAATGTGTGCTTAAGCATGTGTACATTCCTCTCT-TACCTATAATGGTACC-3' (i.e. SEQ ID NO.163) were designed. Plasmid pP43NMK was used as a template and a plasmid fragment was obtained by reverse amplification by PCR. Finally, the recombinant plasmid was constructed by Gibson Assembly Clonging Kit (New England Biolabs), and it was verified that the construction of the recombinant pP43NMK-NO132-GFP plasmid was successful by sequencing.

2. Construction of Recombinant pP43NMK-NO138-GFP Plasmid Bacillus Subtilis

The constructed pP43NMK-NO138-GFP plasmid was transformed into a wild type strain of Bacillus subtilis 168. Primers yz_zong-p43NMK_F: 5'-TTCTTGCT-GAGTCTGGCTTTCG-3' (i.e. SEQ ID NO.156) and yz_zong-p43NMK_R: 5'-CGGCTCGTATGTTGTGTG-GAAT-3' (i.e. SEQ ID NO.157) were used to select transformants for colony PCR, and it was verified that the construction of the recombinant Bacillus subtilis successful was when a 1.8 kb band appeared.

3. Expression of green fluorescent protein in engineering bacteria after addition of N-terminal sequence Seeds of successfully constructed recombinant Bacillus subtilis cultured at 37° C., 200 rpm for 10 h were transferred to the fermentation medium according to an inoculum size of 10% (v/v), and cultured at 37° C., 200 rpm for 20 h.

Figure 5:
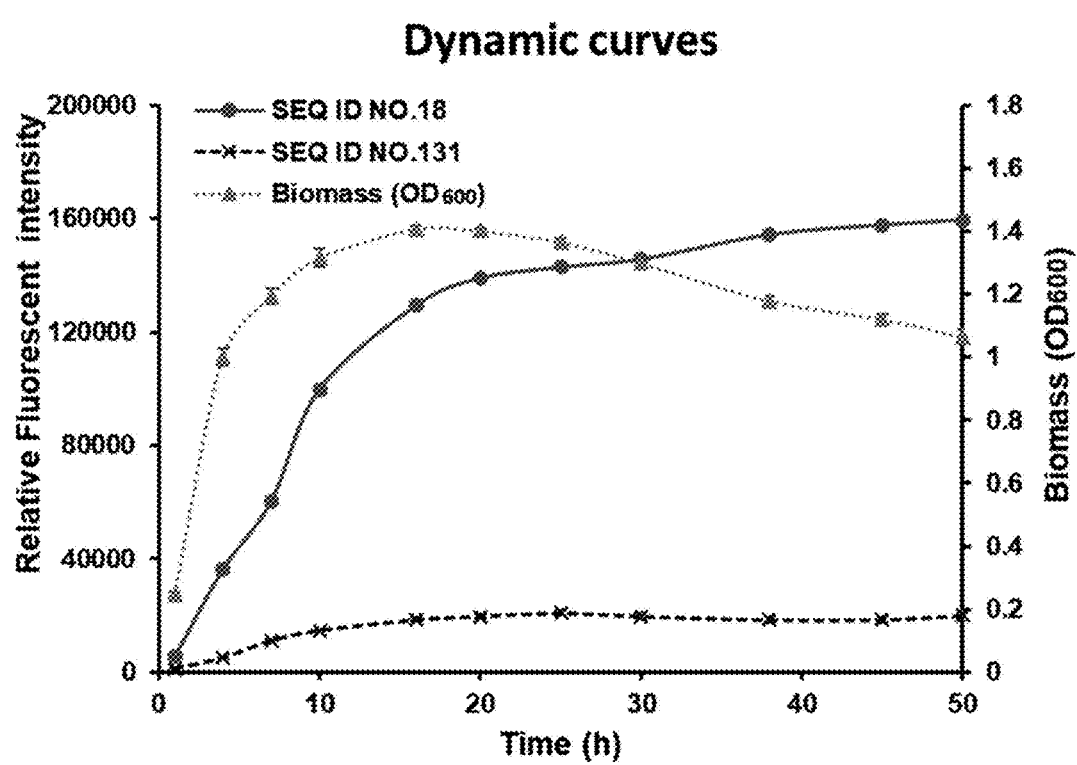
FIG. 5 shows the comparison of the effects of the original N-terminal sequence as shown in SEQ ID NO.18 with the effects of the N-terminal sequence element as shown in SEQ ID NO.131 on protein expression.

Under the same conditions, if the original N-terminal sequence as shown in SEQ ID NO.18 is added, the final fluorescent intensity change curve is not coupled to growth; while after the N-terminal sequence element as shown in SEQ ID NO.131 is added, it was measured that the fluorescent intensity is coupled to growth, as shown in FIG. 5.

Figure 6:
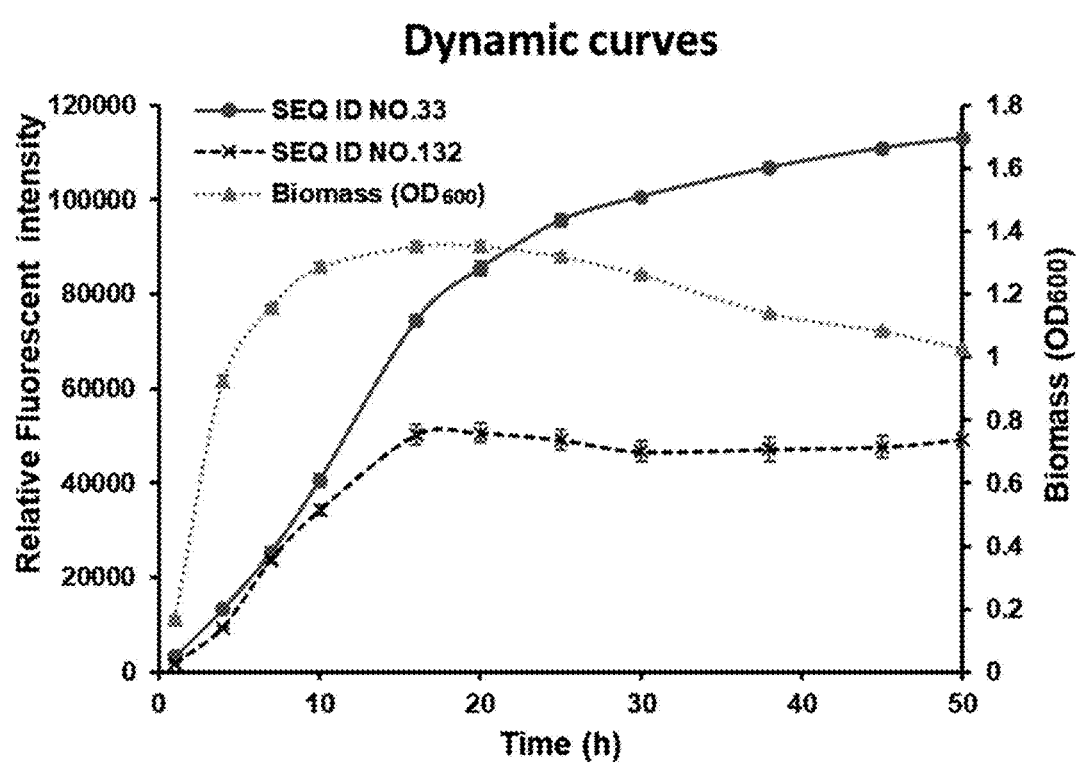
FIG. 6 shows the comparison of the effects of the original N-terminal sequence as shown in SEQ ID NO.33 with the effects of the N-terminal sequence element as shown in SEQ ID NO.132 on protein expression.

Under the same conditions, if the original N-terminal sequence as shown in SEQ ID NO.33 is added, the final fluorescent intensity change curve is not coupled to growth; while after the N-terminal sequence element as shown in SEQ ID NO.132 is added, it was measured that the fluorescent intensity is coupled to growth, as shown in FIG. 6.

Figure 7:
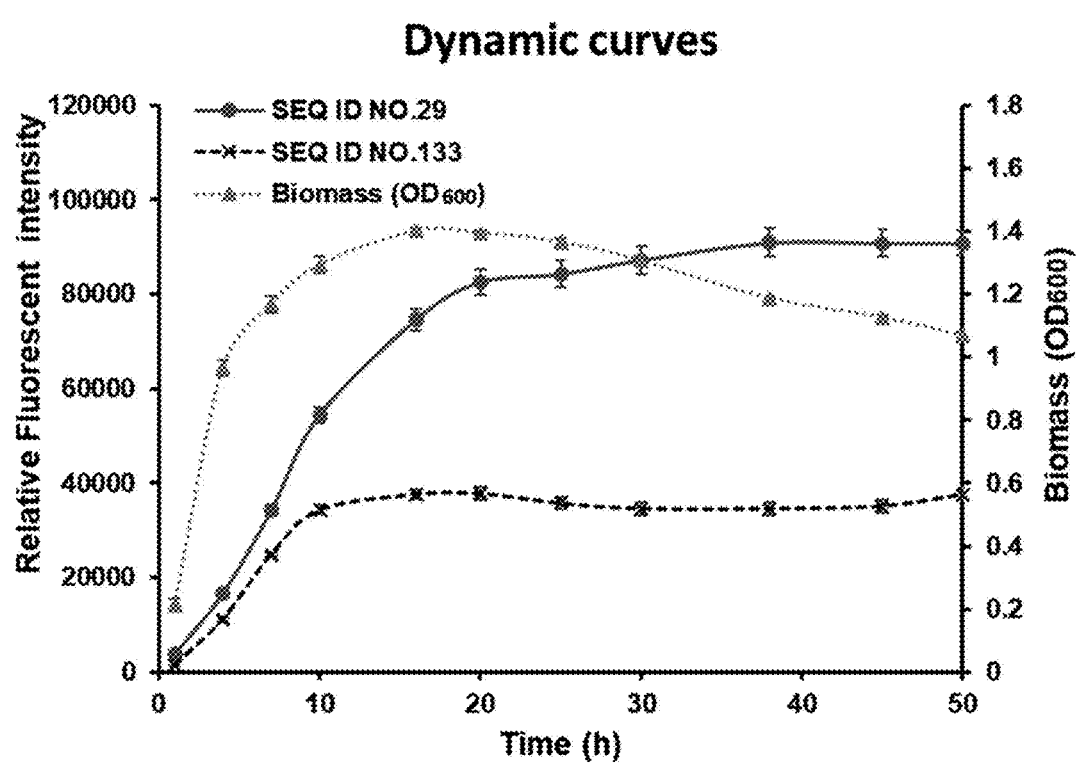
FIG. 7 shows the comparison of the effects of the original N-terminal sequence as shown in SEQ ID NO.29 with the effects of the N-terminal sequence element as shown in SEQ ID NO.133 on protein expression.

Under the same conditions, if the original N-terminal sequence as shown in SEQ ID NO.29 is added, the final fluorescent intensity change curve is not coupled to growth; while after the N-terminal sequence element as shown in SEQ ID NO.133 is added, it was measured that the fluorescent intensity is coupled to growth, as shown in FIG. 7.

Figure 8:
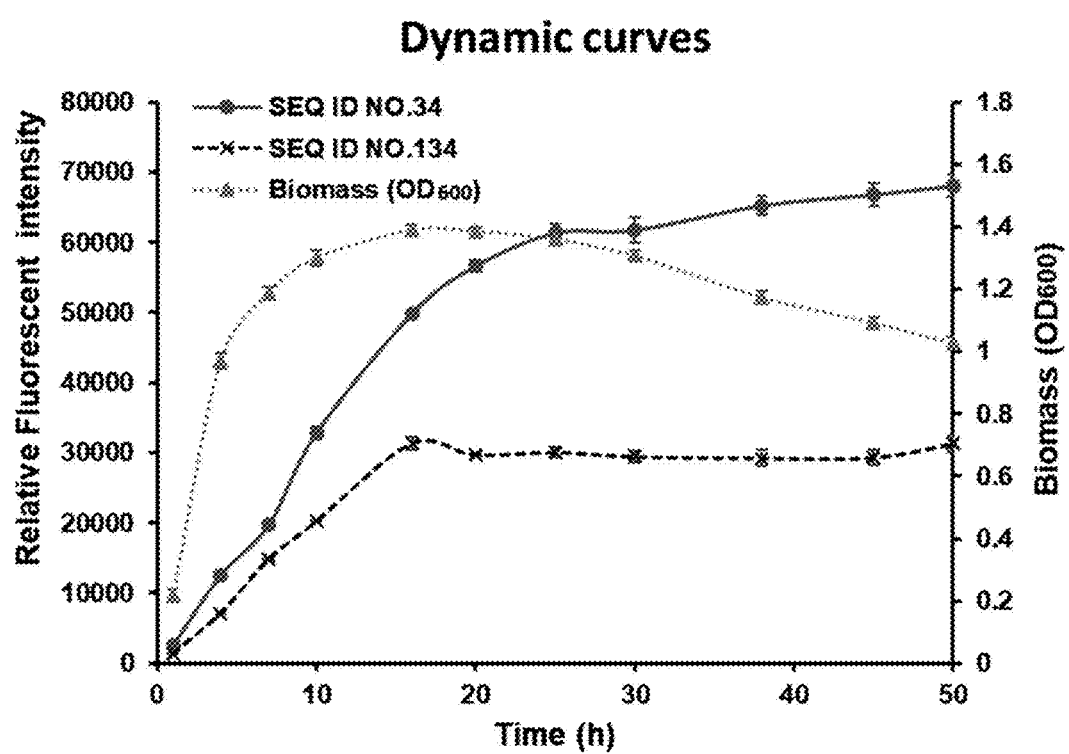
FIG. 8 shows the comparison of the effects of the original N-terminal sequence as shown in SEQ ID NO.34 with the effects of the N-terminal sequence element as shown in SEQ ID NO.134 on protein expression.

Under the same conditions, if the original N-terminal sequence as shown in SEQ ID NO.34 is added, the final fluorescent intensity change curve is not coupled to growth; while after the N-terminal sequence element as shown in SEQ ID NO.134 is added, it was measured that the fluorescent intensity is coupled to growth, as shown in FIG. 8.

Figure 9:
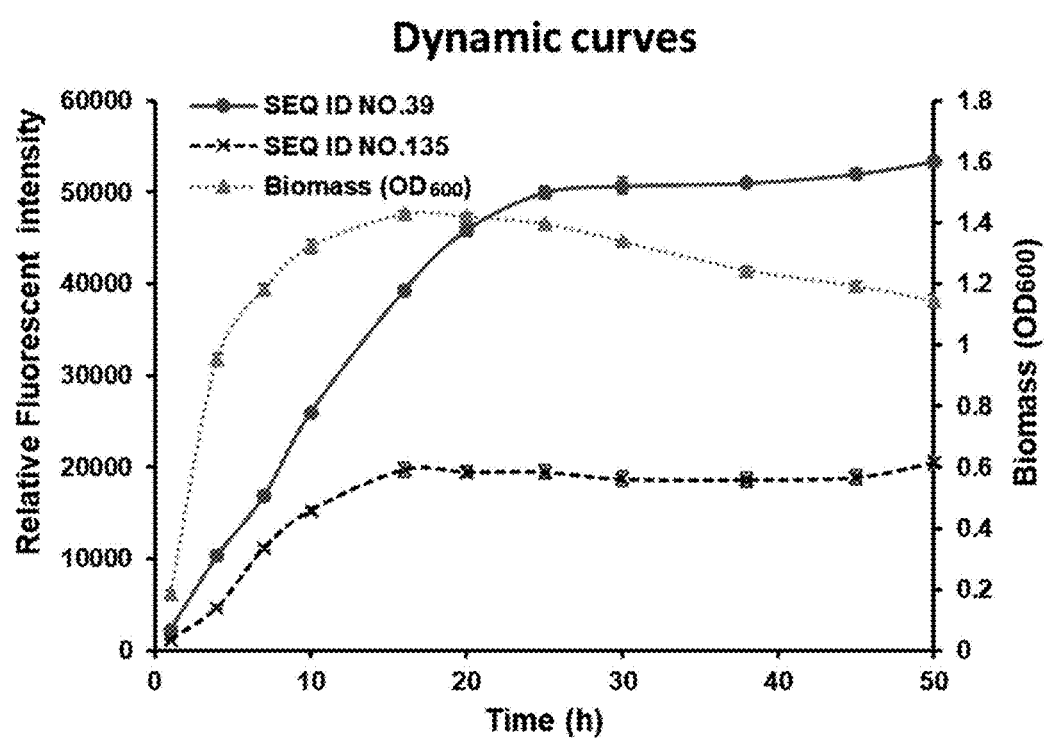
FIG. 9 shows the comparison of the effects of the original N-terminal sequence as shown in SEQ ID NO.39 with the effects of the N-terminal sequence element as shown in SEQ ID NO.135 on protein expression.

Under the same conditions, if the original N-terminal sequence as shown in SEQ ID NO.39 is added, the final fluorescent intensity change curve is not coupled to growth; while after the N-terminal sequence element as shown in SEQ ID NO.135 is added, it was measured that the fluorescent intensity is coupled to growth, as shown in FIG. 9.

Figure 10:
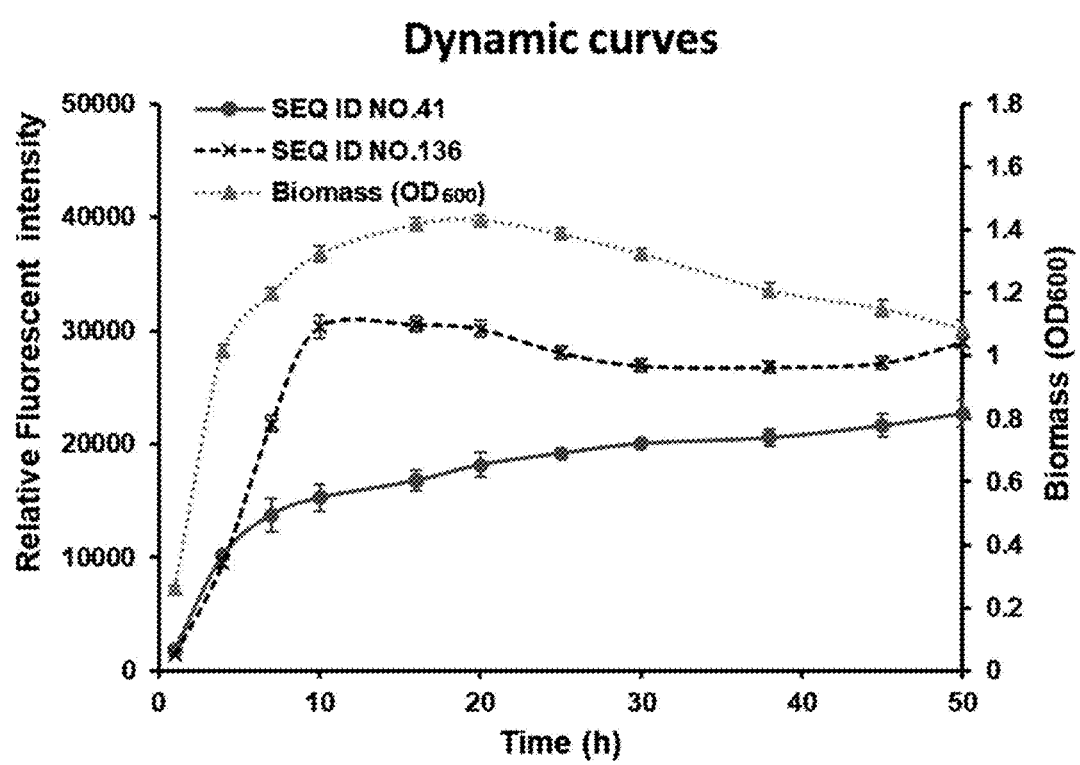
FIG. 10 shows the comparison of the effects of the original N-terminal sequence as shown in SEQ ID NO.41 with the effects of the N-terminal sequence element as shown in SEQ ID NO.136 on protein expression.

Under the same conditions, if the original N-terminal sequence as shown in SEQ ID NO.41 is added, the final fluorescent intensity change curve is not coupled to growth; while after the N-terminal sequence element as shown in SEQ ID NO.136 is added, it was measured that the fluorescent intensity is coupled to growth, as shown in FIG. 10.

Figure 11:
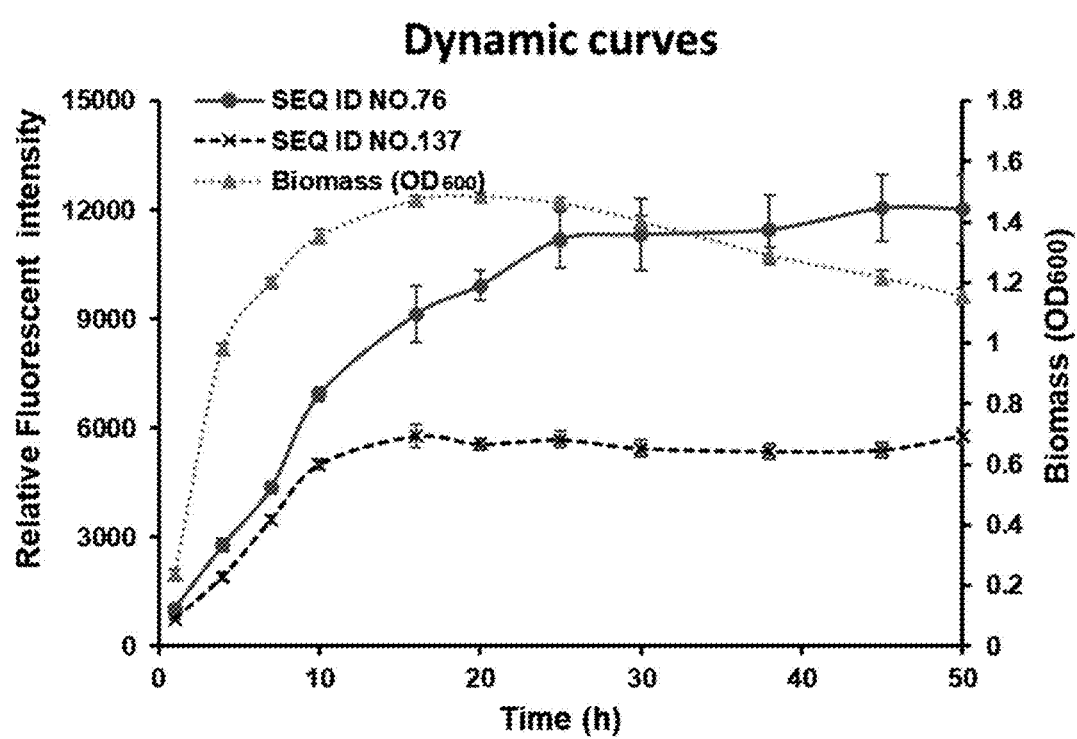
FIG. 11 shows the comparison of the effects of the original N-terminal sequence as shown in SEQ ID NO.76 with the effect of the N-terminal sequence element as shown in SEQ ID NO.137 on protein expression.

Under the same conditions, if the original N-terminal sequence as shown in SEQ ID NO.76 is added, the final fluorescent intensity change curve is not coupled to growth; while after the N-terminal sequence element as shown in SEQ ID NO.137 is added, it was measured that the fluorescent intensity is coupled to growth, as shown in FIG. 11.

The N-terminal sequence elements as shown in SEQ ID NO.131-137 was respectively added to the N-terminal of the GFP nucleotide sequence of the protein of interest, to verify the effects on the expression of the protein. The results are shown in Table 6.

TABLE 6

Increase of protein expression by addition of 7 artificially designed N-terminal sequence elements

| | Fermentation time: | | | | | |
|---|---|---|---|---|---|---|
| | 4 h | | | 20 h | | |
| N-terminal sequence number | Average fluorescent intensity | Error | Gain | Average fluorescent intensity | Error | Gain |
| SEQ ID NO. 131 | 5004.60 | 200.75 | 0.97 | 19761.00 | 512.97 | 0.41 |
| SEQ ID NO. 132 | 9422.25 | 276.65 | 1.83 | 50650.67 | 2052.89 | 1.05 |
| SEQ ID NO. 133 | 11164.25 | 418.75 | 2.16 | 37814.25 | 1281.37 | 0.78 |
| SEQ ID NO. 134 | 7152.60 | 120.61 | 1.39 | 29728.60 | 207.00 | 0.62 |
| SEQ ID NO. 135 | 4700.60 | 190.81 | 0.91 | 19497.20 | 578.99 | 0.40 |
| SEQ ID NO. 136 | 9504.50 | 427.54 | 1.84 | 30170.00 | 702.68 | 0.63 |
| SEQ ID NO. 137 | 1916.80 | 124.38 | 0.37 | 5567.80 | 156.86 | 0.12 |

Comparative Example Construction of a Control Group Without Specific N-Terminal Sequence The composition of the recombinant control plasmid is that the green fluorescent protein (GFP) gene is directly inserted after the P43 promoter of the Pp43NMK plasmid. Primers rh_Ctr-0.75k_p43NMK-GFP_F: 5'-ACACAT-GAGTAAAGGAGAAGAACTTTTCACTGGAGTTGT-CCCA-3' (i.e. SEQ ID NO.158), and rh_Ctr-0.75k_p43NMK-GFP_R: 5'-TACGCCAAGCTTTCATC-ACTATTTGTATAGTTCATCCATGCCATGTGTAAT-CCCAGCAG-3' (i.e. SEQ ID NO.153) were designed, Escherichia coli containing the green fluorescent protein (GFP, GenBank: AF324408.1) gene was used as a template, and a green fluorescent protein fragment was obtained by colony PCR. Primers fx_ctr-6.7k_p43NMK-GFP_F: 5'-AGTGATGAAAGCTTGGCGTAATCATGGTCAT-AGCTGTTT-3' (i.e. SEQ ID NO.154), and fx_ctr-6.7k_p43NMK-GFP_R: 5'-CTTCTCCTTTACTCATGT-GTACATTCCTCTCTTACCTATAATGGTACCGCTAT-CACTT-3' (i.e. SEQ ID NO. 164) were designed. Plasmid pP43NMK was used as a template and a plasmid fragment was obtained by reverse amplification by PCR. Finally, the recombinant plasmid by Gibson Assembly Clonging Kit (New England Biolabs) was constructed. After verifying that the construction of the recombinant pP43NMK-Ctr-GFP plasmid was successful by sequencing, a Bacillus subtilis 168 wild type was transformed. It was verified that the plasmid is successfully transformed by colony PCR.

If transferring seeds of the recombinant Bacillus subtilis cultured at 37° C., 750 rpm in a 700 μL LB medium and in a 96-well deep-well plate for 9 h to a 190 μL LB medium according to an inoculum size of 5% (v/v) and culturing the seeds at 37° C., 750 rpm for 4 h or 20 h. Finally, the fluorescent intensity measured in the fermentation broth after 4 h is 5159, which is only 14% of the fluorescent intensity after addition of the N-terminal sequence (i.e. SEQ ID NO.18) of YdbP protein; the fluorescent intensity measured in the fermentation broth after 20 h is 48181, which is only 35% of the fluorescent intensity after addition of the N-terminal sequence of YdbP protein.

Although the present disclosure has been disclosed above in the preferred examples, it is not intended to limit the present disclosure. Any modifications and variations can be made without departing from the spirit and scope of the present disclosure by any person skilled in the art, and the scope of the present disclosure shall be determined by the scope of the appended claims.

What is claimed is:

1. A method for regulating expression of a protein in *Bacillus subtilis*, comprising:
    modifying a gene encoding the protein by adding upstream thereto nucleotide sequence SEQ ID NO:18 to obtain a modified gene encoding a recombinant protein,
    transferring the modified gene encoding the recombinant protein into an expression vector, and
    transfecting *Bacillus subtilis* with the expression vector for expression of the recombinant protein, and inducing expression of the expression vector.

2. The method according to claim 1, wherein the *Bacillus subtilis* strain is any one or more of: *Bacillus subtilis* 168, *Bacillus subtilis* WB400, *Bacillus subtilis* WB600, and *Bacillus subtilis* WB800.

3. The method according to claim 1, wherein the expression vector comprises pP43NMK.

4. The method according to claim 1, wherein the protein comprises an enzyme.

5. A vector comprising the modified gene encoding the recombinant protein of claim 1.

* * * * *